(12) United States Patent
Siddiqui-Jain et al.

(10) Patent No.: US 9,758,539 B2
(45) Date of Patent: Sep. 12, 2017

(54) ALVOCIDIB PRODRUGS HAVING INCREASED BIOAVAILABILITY

(71) Applicant: Tolero Pharmaceuticals, Inc., Lehi, UT (US)

(72) Inventors: Adam Siddiqui-Jain, South Jordan, UT (US); David J. Bearss, Alpine, UT (US)

(73) Assignee: Tolero Pharmaceuticals, Inc., Lehi, UT (US)

( * ) Notice: Subject to any disclaimer, the term of this patent is extended or adjusted under 35 U.S.C. 154(b) by 0 days.

(21) Appl. No.: 15/158,206

(22) Filed: May 18, 2016

(65) Prior Publication Data

US 2016/0340376 A1 Nov. 24, 2016

Related U.S. Application Data

(60) Provisional application No. 62/163,188, filed on May 18, 2015.

(51) Int. Cl.

| | | |
|---|---|---|
| *C07D 211/40* | (2006.01) |
| *C07F 9/6558* | (2006.01) |
| *C07D 311/30* | (2006.01) |
| *C07D 311/22* | (2006.01) |
| *C07D 405/04* | (2006.01) |

(52) U.S. Cl.
CPC ........ *C07F 9/65586* (2013.01); *C07D 311/22* (2013.01); *C07D 311/30* (2013.01); *C07D 405/04* (2013.01)

(58) Field of Classification Search
CPC .... C07D 311/22; C07D 311/30; C07D 405/04
USPC ...................................................... 546/216
See application file for complete search history.

(56) References Cited

U.S. PATENT DOCUMENTS

| | | |
|---|---|---|
| 6,087,366 A | 7/2000 | Park et al. |
| 6,225,473 B1 | 5/2001 | Breipohl et al. |
| 6,576,647 B2 | 6/2003 | Bafus et al. |
| 6,821,990 B2 | 11/2004 | Kesseler |
| 7,868,133 B2 | 1/2011 | Korsmeyer et al. |
| 8,168,755 B2 | 5/2012 | Cardone et al. |
| 8,221,966 B2 | 7/2012 | Letai |
| 2008/0027105 A1 | 1/2008 | Suarez et al. |
| 2011/0130309 A1 | 6/2011 | Cardone |
| 2011/0251240 A1 | 10/2011 | Suarez et al. |
| 2012/0225851 A1 | 9/2012 | Cardone et al. |
| 2014/0080838 A1 | 3/2014 | Wendel et al. |
| 2014/0303167 A1 | 10/2014 | Choidas et al. |
| 2015/0150869 A1 | 6/2015 | Cardone et al. |
| 2015/0301053 A1 | 10/2015 | Pierceall et al. |
| 2015/0352097 A1 | 12/2015 | Cardone et al. |
| 2016/0303101 A1 | 10/2016 | Warner et al. |

FOREIGN PATENT DOCUMENTS

| | | |
|---|---|---|
| WO | 03/028001 A2 | 4/2003 |
| WO | 2004/022580 A2 | 3/2004 |
| WO | 2016/115105 A1 | 7/2006 |
| WO | 2006/101846 A1 | 9/2006 |
| WO | 2007/123791 A2 | 11/2007 |
| WO | 2012/122370 A2 | 9/2012 |
| WO | 2013/082660 A1 | 6/2013 |
| WO | 2013/170176 A2 | 11/2013 |
| WO | 2014/047342 A1 | 3/2014 |
| WO | 2014/066848 A1 | 5/2014 |
| WO | 2015/010094 A1 | 1/2015 |
| WO | 2015/017788 A1 | 2/2015 |
| WO | 2015/042249 A1 | 3/2015 |
| WO | 2015/066305 A1 | 5/2015 |
| WO | 2016/073913 A1 | 5/2016 |

OTHER PUBLICATIONS

Almarzooqi et al., "Comparison of Peripheral Blood versus Bone Marrow Blasts Immunophenotype in Pediatric Acute Leukemias," *Ibnosina Journal of Medicine and Biomedical Sciences* 3(6):195-204, 2011.

Azevedo Jr. et al., "Structural basis for inhibition of cyclin-dependent kinase 9 by flavopiridol," *Biochemical and Biophysical Research Communications* 293:566-571, 2002.

Byrd et al., "Flavopiridol Induces Apoptosis in Chronic Lymphocytic Leukemia Cells Via Activation of Caspase-3 Without Evidence of bcl-2 Modulation or Dependence on Functional p53," *Blood* 92(10):3804-3816, Nov. 1998.

Chonghaile et al., "Mimicking the BH3 domain to kill cancer cells," *Oncogene* 27:S149-S157, 2009.

Czech et al., "Antitumoral activity of flavone L 86-8275," *International Journal of Oncology* 6:31-36, 1995.

(Continued)

*Primary Examiner* — Kevin E Weddington
(74) *Attorney, Agent, or Firm* — Seed IP Law Group LLP

(57) ABSTRACT

Compounds having the following structure (I):

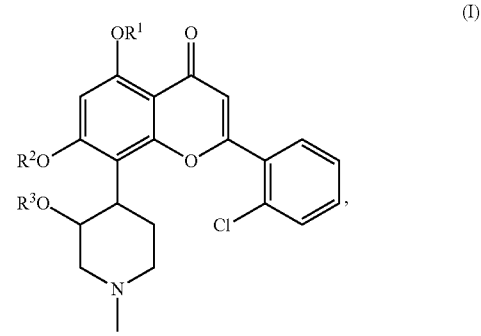

or a stereoisomer, tautomer or pharmaceutically acceptable salt thereof, wherein one of $R^1$, $R^2$ or $R^3$ is $-P(=O)(OH)_2$, and the other two of $R^1$, $R^2$ and $R^3$ are each H, are provided. Pharmaceutical compositions comprising the compounds, and methods for use of the compounds for treating diseases associated with overexpression of a cyclin-dependent kinase (CDK) are also provided.

13 Claims, 13 Drawing Sheets

(56) References Cited

OTHER PUBLICATIONS

Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.

Falkenberg et al., "Histone deacetylases and their inhibitors in cancer, neurological diseases and immune disorder," *Nature Reviews Drug Discovery* 13:673-691, Sep. 2014, 20 pages. (Addendum included).

Filippakopoulos et al., "Targeting bromodomains: epigenetic readers of lysine acetylation," *Nature Reviews Drug Discovery* 13:337-356, May 2014.

Fiskus et al., "Highly Active Combination of BRD4 Antagonist and Histone Deacetylase Inhibitor against Human Acute Myelogenous Leukemia Cells," *Molecular Cancer Therapeutics* 13(5):1142-1154, May 2014.

Hirst et al., "Application of Non-Parametric Regression to Quantitative Structure-Activity Relationships," *Bioorganic & Medicinal Chemistry* 10:1037-1041, 2002.

Labi et al., "Targeting the Bcl-2-regulated apoptosis pathway by BH3 mimetics: a breakthrough in anticancer therapy?," *Cell Death and Differentiation* 15:977-987, 2008.

Letai et al., "Distinct BH3 domains either sensitize or activate mitochondrial apoptosis, serving as prototype cancer therapeutics," *Cancer Cell* 2:183-192, 2002.

Moore et al., "BH3 profiling—measuring integrated function of the mitochondrial apoptotic pathway to predict cell fate decisions," *Cancer Letters* 332(2):202-205, 2013. (10 pages).

Naik et al., "An Antiinflammatory Cum Immunomodulatory Piperidinylbenzopyranone from *Dysoxylum Binectariferum:* Isolation, Structure and Total Synthesis," *Tetrahedron* 44(7):2081-2086, 1988.

Rezaei et al., "Leukemia markers expression of peripheral blood vs. bone marrow blasts using flow cytometry," *Medical Science Monitor* 9(8):CR359-CR362, 2003.

Ryan et al., "BH3 Profiling in Whole Cells by Fluorimeter of FACS," *Methods* 61(2):156-164, 2013. (22 pages).

Sedlacek et al., "Flavopiridol (L86 8275; NSC 649890), a new kinase inhibitor for tumor therapy," *International Journal of Oncology* 9:1143-1168, 1996.

Warner et al., "Predicting Response to Alvocidib by Mitochondrial Profiling,"U.S. Appl. No. 15/134,051, filed Apr. 20, 2016, 87 pages.

Yang et al., "Bone marrow stroma-mediated resistance to FLT3 inhibitors in FLT3-ITD AML is mediated by persistent activation of extracellular regulated kinase," *British Journal of Haematology* 164:61-72, 2014.

Zeng et al., "Targeting the leukemia microenvironment by CXCR4 inhibition overcomes resistance to kinase inhibitors and chemotherapy in AML," *Blood* 113(24):6215-6224, 2009.

Bose et al., "Mcl-1 as a therapeutic target in acute myelogenous leukemia (AML)," *Leukemia Research Reports* 2:12-14, 2013.

Byrd et al., "Flavopiridol administered using a pharmacologically derived schedule is associated with marked clinical efficacy in refractory, genetically high-risk chronic lymphocytic leukemia," *Blood* 109(2):399-404, Jan. 2007.

Byrd et al., "Chronic Lymphocytic Leukemia," *American Society of Hematology Education Program Book* :163-183, 2004.

Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104, Abstract No. 341, 2004, 2 pages.

Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104, Abstract No. 3485, 2004, 2 pages.

Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clinical Cancer Research* 11(11):4176-4181, Jun. 2005.

Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, Jul. 1996.

Chao et al., "Flavopiridol Inactivates P-TEFb and Blocks Most RNA II Transcription in vitro," *The Journal of Biological Chemistry* 276(34):31793-31799, Aug. 2001.

Chao et al., "Flavopiridol Inhibits P-TEFb and Blocks HIV-1 Replication," *The Journal of Biological Chemistry* 275(37):28345-28348, Sep. 2000.

Cheson et al., "National Cancer Institute-Sponsored Working Group Guidelines for Chronic Lymphocytic Leukemia: Revised Guidelines for Diagnosis and Treatment," *Blood* 87(12):4990-4997, Jun. 1996.

Conaway et al., "The Mediator Complex and Transcription Elongation," *Biochim Biophys Acta* 1829(1):69-75, 2013.

De Azevedo, Jr et al., "Structural basis for inhibition of cyclin-dependent kinase 9 by flavopiridol," *Biochemical and Biophysical Research Communications* 293:566-571, 2002.

Dettman et al., "Abstract 3400: Mitochondrial profiling in AML patients treated with an Alvocidib containing regimen reveals MCL1 dependency in responder bone marrow," *Cancer Research* 75, Abstract No. 3400, Aug. 2015, 2 pages.

Guha, "Cyclin-dependent kinase inhibitors move into Phase III," *Nature Reviews Drug Discovery* 11:892-894, Dec. 2012.

Hnisz et al., "Super-Enhancers in the Control of Cell Identity and Disease," *Cell* 155:934-947, Nov. 2013.

Innocenti et al., "Flavopiridol Metabolism in Cancer Patients is Associated with the Occurrence of Diarrhea," *Clinical Cancer Research* 6:3400-3405, Sep. 2000.

Keating et al., "Therapeutic role of alemtuzumab (Campath-1H) in patients who have failed fludarabine: results of a large international study," *Blood* 99(10):3554-3561, May 2002.

Kitada et al., "Protein kinase inhibitors flavopiridol and 7-hydroxystaurosporine down-regulate antiapoptosis proteins in B-cell chronic lymphocytic leukemia," *Blood* 96(2):393-397, Jul. 2000.

König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90(11):4307-4312, Dec. 1997.

Lin et al., "Flavopiridol given as a 30-min intravenous (IV) bolus followed by a 4-hr continuous IV infusion (CIVI) results in clinical activity and tumor lysis in refractory chronic lymphocytic leukemia (CLL)," *Journal of Clinical Oncology* 22(14S), Abstract No. 6564, Jul. 2004, 1 page.

Lin et al., "Seventy-Two Hour Continuous Infusion Flavopiridol in Relapsed and Refractory Mantle Cell Lymphoma," *Leukemia & Lymphoma* 43(4):793-797, 2002.

Lovén et al., "Selective Inhibition of Tumor Oncogenes by Disruption of Super-Enhancers," *Cell* 153(2):320-334, Apr. 2013.

Lozanski et al., "Alemtuzumab is an effective therapy for chronic lymphocytic leukemia with p53 mutations and deletions," *Blood* 103(9):3278-3281, May 2004.

Murthi et al., "Structure-Activity Relationship Studies of Flavopiridol Analogues," *Bioorganic & Medicinal Chemistry Letters* 10:1037-1041, 2000.

Oscier et al., "Multivariate analysis of prognostic factors in CLL: clinical stage, IGVH gene mutational status, and loss or mutation of the p53 gene are independent prognostic factors," *Blood* 100(4):1177-1184, Aug. 2002.

Parker et al., "Early Induction of Apoptosis in Hematopoietic Cell Lines After Exposure to Flavopiridol," *Blood* 91(2):458-465, Jan. 1998.

Perkins et al., "Frequency and Type of Serious Infections in Fludarabine-Refractory B-Cell Chronic Lymphocytic Leukemia and Small Lymphocytic Lymphoma," *Cancer* 98(7):2033-2039, Apr. 2002.

Pierceall et al., "Mcl-1 Dependence Predicts Response to Vorinostat and Gemtuzumab Oxogamicin in Acute Myeloid Leukemia," *Leukemia Research* 38(5):564-568, 2014.

Pierceall et al., "Mitochondrial Priming of Chronic Lymphocytic Leukemia Patients Associates Bcl-$x_L$ Dependence with Alvocidib Response," *Leukemia* 28(11):2251-2254, Nov. 2014.

(56) References Cited

OTHER PUBLICATIONS

Rudek et al., "Clinical Pharmacology of Flavopiridol Following a 72-Hour Continuous Infusion," *The Annals of Pharmacotherapy* 37:1369-1374, Oct. 2003.
Senderowicz et al., "Preclinical and Clinical Development of Cyclin-Dependent Kinase Modulators," *Journal of the National Cancer Institute* 92(5):376-387, Mar. 2000.
Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, Jun. 2001.
Smith et al., "An alvocidib-containing regimen is highly effective in AML patients through a mechanism dependent on MCL1 expression and function," 2015 American Society of Clinical Oncology Annual Meeting, May 29-Jun. 2, 2015, Chicago, IL, 3 pages.
Smith et al., "Enhancer biology and enhanceropathies," *Nature Structural & Molecular Biology* 21(3):210-219, Mar. 2014.
Sturm et al., "Mutation of p53 and consecutive selective drug resistance in B-CLL occurs as a consequence of prior DNA-damaging chemotherapy," *Cell Death and Differentiation* 10:477-484, 2003.
Thornton et al., "Characterisation of TP53 abnormalities in chronic lymphocytic leukemia," *The Hematology Journal* 5:47-54, 2004.
Thornton et al., "High dose methylprednisolone can induce remissions in CLL patients with p53 abnormalities," *Annals of Hematology* 82:759-765, 2003.
Venkat, "Flavopiridol: A Drug that May Save Lives," *CLL Topics*, Jun. 6, 2004, archived screenshot of webpage retrieved from https://web.archive.org/web/20060615112217/http://clltopics.org/Chemo/flavopiridol.htm on Aug. 16, 2016, 7 pages.
Ververis et al., "Histone deacetylase inhibitors (HDACIs): multitargeted anticancer agents," *Biologics: Targets and Therapy* 7:47-60, Feb. 2013.
Yang et al., "A novel liposomal formulation of flavopiridol," *International Journal of Pharmaceutics* 365:170-174, 2009.
Zhai et al., "Clinical pharmacology and pharmacogenetics of flavopiridol 1-h i.v. infusion in patients with refractory neoplasms," *Anti-Cancer Drugs* 14:125-135, 2003.
Dettman et al., Context Dependent Diagnostics Test for Guiding Cancer Treatment, U.S. Appl. No. 62/102,499, filed Jan. 12, 2015, 71 pages.
Bearss, "NOXA Priming—Predicitive Biomarker for Patients With Acute Myeloid Leukemia to Improve Treatment Outcomes," Harvard Business School Challenge—Open Forum—Precision Trials Challenge, Mar. 11, 2016, retrieved from https://openforum.hbs.org/challenge/precision-medicine/submit-ideas/noxa-priming-predictive-biomarker-for-patients-with-acute-myeloid-leukemia-to-improve-treatment-outcomes on Dec. 8, 2016, 7 pages.
Geserick et al., "The ratio of Mcl-1 and Noxa determines ABT737 resistance in squamous cell carcinoma of the skin," *Cell Death and Disease* 5:e1412, 2014, 14 pages.
Tolero Pharamaceuticals, "Making Meaningful Medicines," Jefferies 2016 Healthcare Conference, 31 pages.
Vo et al., "Relative Mitochondrial Priming of Myeloblasts and Normal HSCs Determines Chemotherapeutic Success in AML," *Cell* 151:344-355, Oct. 2012.

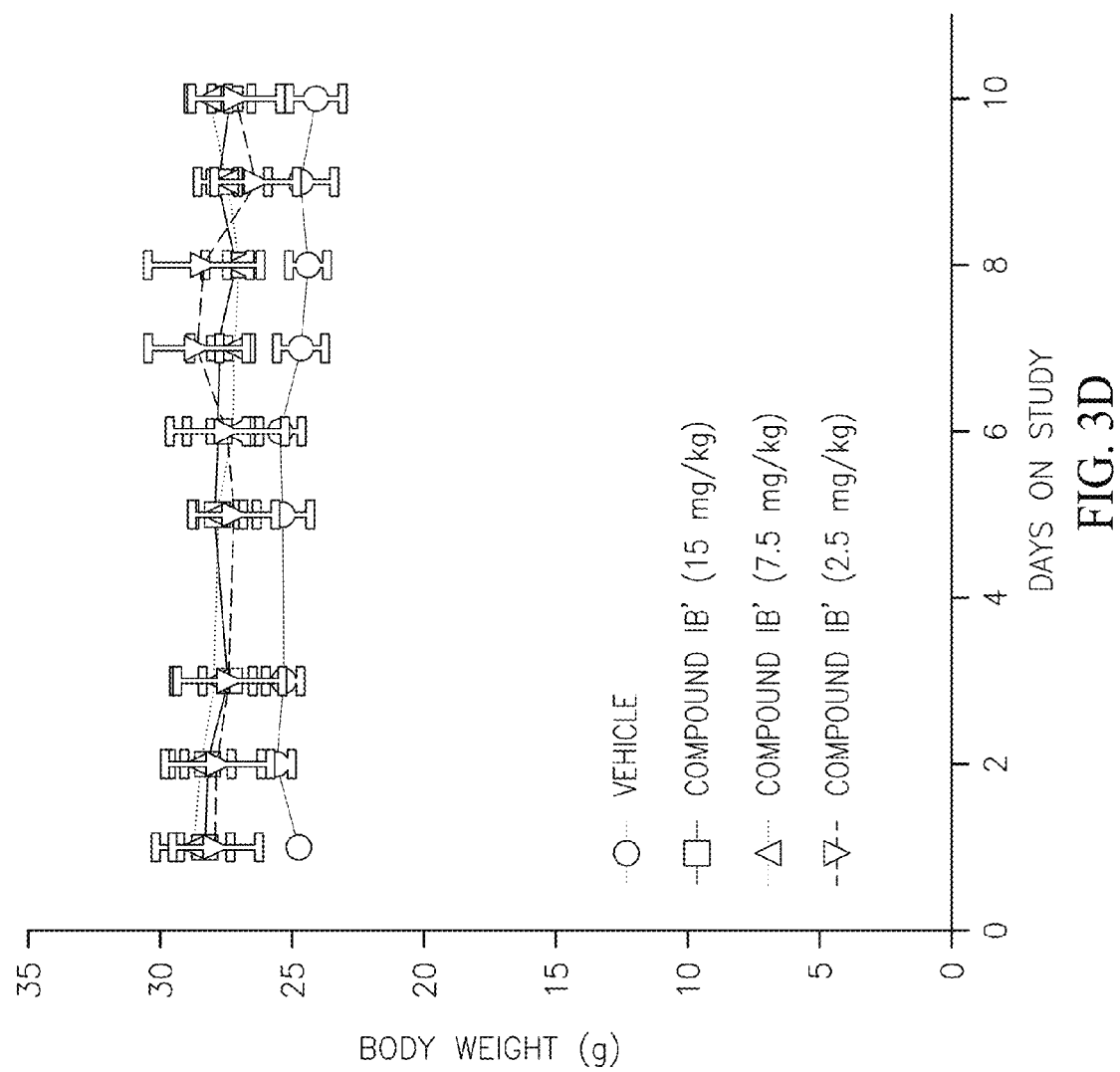

ALVOCIDIB PRODRUGS HAVING INCREASED BIOAVAILABILITY

BACKGROUND

Technical Field

The present invention is generally directed to phosphate prodrugs of alvocidib and use of the same for treatment of cancer.

Description of the Related Art

Cyclin-dependent kinases (CDKs) are important regulators that control the timing and coordination of the cell cycle. CDKs form reversible complexes with their obligate cyclin partners to control transition through key junctures in the cell cycle. For example, the activated CDK4-cyclin D1 complex controls progression through the G1 phase of the cell cycle, while the CDK1-cyclin B1 complex controls entry into the mitotic phase of the cell cycle. Endogenous cyclin dependent kinase inhibitory proteins (CDKIs) are known to bind either the CDK or cyclin component and inhibit the kinase activity of the complex. In many tumors such as melanomas, pancreatic and esophageal cancers, these natural CDKIs are either absent or mutated. Thus, selective CDK inhibitors may prove to be effective chemotherapeutic agents.

Alvocidib (also known as Flavopiridol) is a synthetic flavone having the following structure:

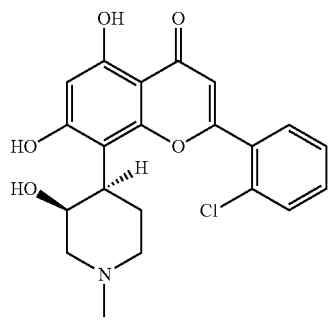

Alvocidib is a potent and selective inhibitor of the CDKs and has antitumor activity against various tumor cells lines, such as human lung carcinoma and breast carcinoma and also inhibits tumor growth in xenograft models. Alvocidib has been shown to induce arrest in both the G1 and G2 phases of the cell cycle and also inhibit polymerase II driven transcription by inhibiting CDK9. By inhibiting CDK9, which forms part of the complex known as the positive transcription elongation factor or P-TEFb, alvocidib treatment reduces the expression of key oncogenes such MYC and key anti-apoptotic proteins such as MCL1. Accordingly, alvocidib is an attractive therapeutic agent for cancer and is currently undergoing clinical trials in relapsed/refractory AML patients.

Oral administration of alvocidib has been limited by gastrointestinal toxicity and limited oral bioavailability. Further, preclinical studies suggest that prolonged exposure may be important for maximizing alvocidib's activity. Accordingly, continuous intravenous infusion schedules have been extensively explored in human trials. Alternative hybrid dosing, including an intravenous bolus dose followed by a slow infusion have also been explored, but to date there have been no reports of orally delivering a therapeutically effective amount of alvocidib.

While progress has been made, there remains a need in the art for increasing the oral bioavailability of alvocidib. The present invention fulfills this need and provides related advantages.

BRIEF SUMMARY

In brief, embodiments of the present invention provide phosphate prodrugs of alvocidib having increased bioavailability relative to the alvocidib parent compound. Accordingly, in one embodiment is provided a compound having the following structure (I):

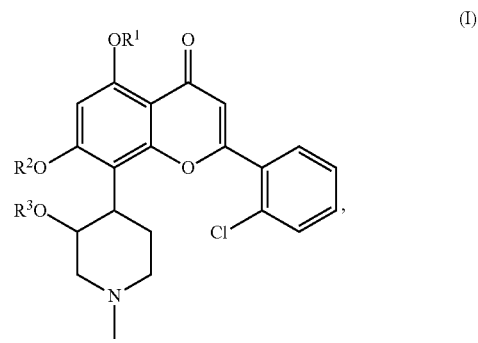

or a stereoisomer, tautomer or pharmaceutically acceptable salt thereof, wherein:
one of $R^1$, $R^2$ or $R^3$ is —P(=O)(OH)$_2$, and the other two of $R^1$, $R^2$ and $R^3$ are each H.

Other embodiments are directed to a pharmaceutical composition comprising a pharmaceutically acceptable carrier or excipient and a compound of structure (I). Methods for use of the compound of structure (I), and pharmaceutical compositions comprising the same, for treatment of a disease associated with overexpression of a cyclin-dependent kinase (CDK) in a mammal in need thereof are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 3A-D show the body weights of mice treated with daily doses (FIG. 3A-B orally, FIG. 3C-D intravenously) of alvocidib or compound IB.

DETAILED DESCRIPTION

Figure 1:
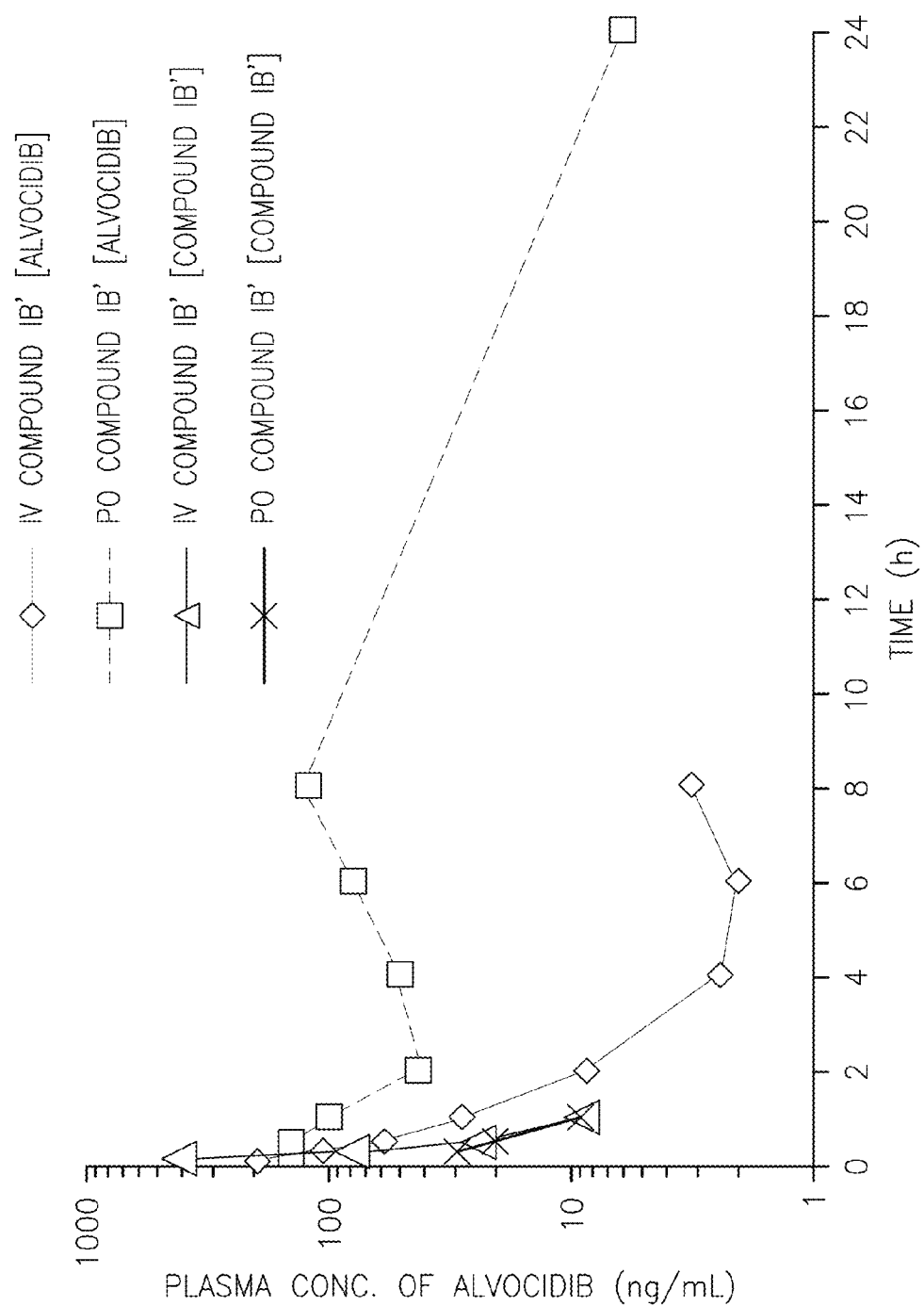
FIG. 1 shows the pharmacokinetic profile of alvocidib and compound IB following the administration of compound IB to Sprague Dawley rats.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Embodiments of the present invention include phosphate prodrugs of alvocidib. "Phosphate" refers to the —OP(=O)(OH)$_2$ moiety. For ease of illustration the phosphate moieties herein are often depicted in the di-protonated form, but also exist in the mono-protonated (—OP(=O)(OH)(O$^-$)) and unprotonated forms (—OP(=O)(O$^-$)$_2$), depending on pH. The mono- and unprotonated forms will typically be associated with a counterion, such that the compounds are in the form of a pharmaceutically acceptable salt. Such mono- and unprotonated forms, and their pharmaceutically acceptable salts, are encompassed within the scope of the inventions, even if not specifically illustrated in the chemical structures.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

A "compound of the invention" refers to a compound of structure (I), and its substructures, as defined herein.

Embodiments of the invention disclosed herein are also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, embodiments of the compounds of the present invention may exist as a hydrate, including a monohydrate, dihydrate, hemihydrate, sesquihydrate, trihydrate, tetrahydrate and the like, as well as the corresponding solvated forms. Embodiments of the compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Mammal" includes humans and both domestic animals such as laboratory animals and household pets (e.g., cats, dogs, swine, cattle, sheep, goats, horses, rabbits), and non-domestic animals such as wildlife and the like.

"Effective amount" or "therapeutically effective amount" refers to that amount of a compound of the invention which, when administered to a mammal, preferably a human, is sufficient to effect treatment, as defined below, of a disease associated with overexpression of a cyclin-dependent kinase (CDK) in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. Embodiments of the present invention contemplate various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments of the present invention include tautomers of any said compounds.

I. Compounds

As noted above, embodiments of the present disclosure are directed to prodrugs of alvocidib having increased bioavailability relative to the parent compound. Surprisingly, experiments performed in support of the present invention demonstrate that a monophosphate analogue of alvocidib has a bioavailability of approximately 1.3 times the parent alvocidib compound when delivered orally to CD-1 mice and more than 8 times that of the related diphosphate prodrugs. The presently disclosed monophosphate compounds are metabolized to alvocidib in vivo and, while not wishing to be bound by theory, it is believed that the increase in bioavailability of alvocidib released from the monophosphate prodrug compared to the alvocidib parent compound is related to a slower rate of metabolism of the prodrug compared to alvocidib. Other expected advantages of the present compounds include increased solubility in typical pharmaceutical formulations, in water and in bodily fluids, and decreased toxicity relative to the alvocidib parent compound when administered orally.

Accordingly, in one embodiment a compound is provided having the following structure (I):

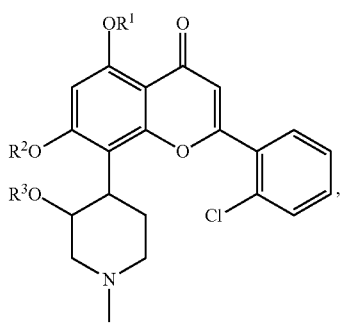

(I)

or a stereoisomer, tautomer or pharmaceutically acceptable salt thereof, wherein:
one of $R^1$, $R^2$ or $R^3$ is —P(=O)(OH)$_2$, and the other two of $R^1$, $R^2$ and $R^3$ are each H.

In certain embodiments, the compound has the following structure (I'):

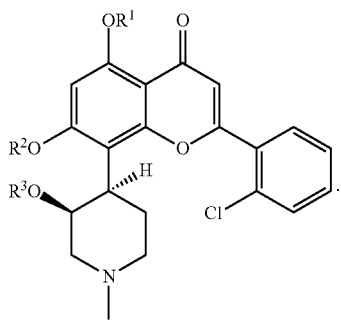

(I')

In some other embodiments, the compound has the following structure (IA):

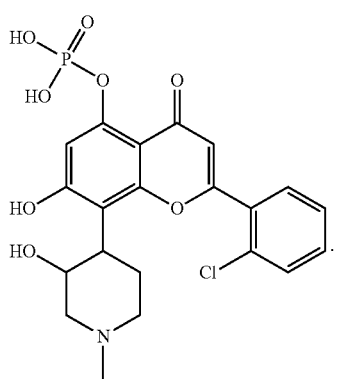

(IA)

In some more embodiments, the compound has the following structure (IA'):

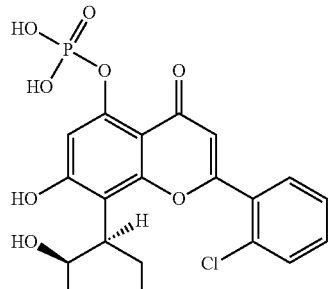

(IA')

In yet other embodiments, the compound has the following structure (IB):

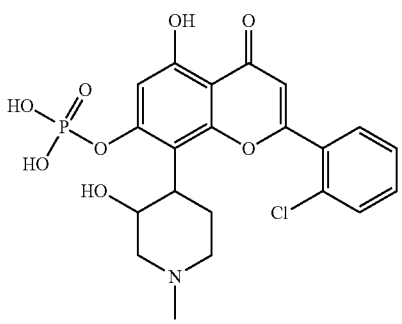

(IB)

In other different embodiments, the compound has the following structure (IB'):

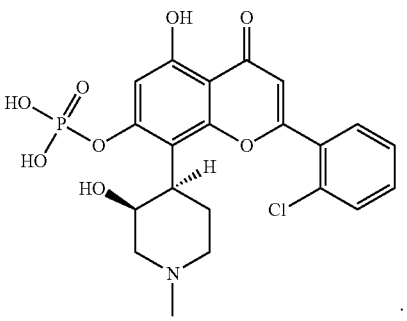

(IB')

In still more embodiments, the compound has the following structure (IC):

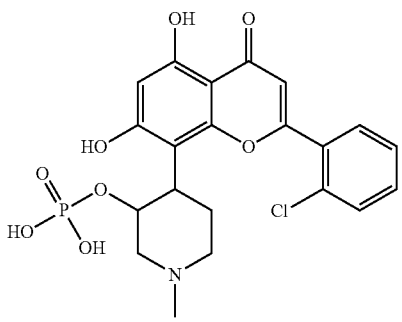

(IC)

In some other different embodiments, the compound has the following structure (IC'):

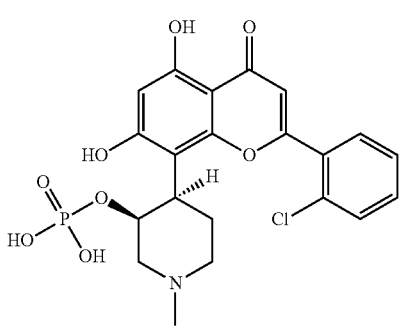

In some embodiments, any of the foregoing compounds are in the form of a pharmaceutically acceptable salt. The salt may be an acid addition salt or a base addition salt. For example, the salt may be an amine salt formed by protonation of the N-methyl piperazine moiety (e.g., HCl salt and the like). In other embodiments, the salt is formed at the phosphate, and the compounds are in the form of mono- or di-salts of the phosphate group (e.g., mono- or disodium phosphate salt and the like). All pharmaceutically acceptable salts of the foregoing compounds are included in the scope of the invention.

Also provided are pharmaceutical compositions comprising a pharmaceutically acceptable carrier or excipient and any of the foregoing compounds (i.e., a compound of structure (I), (I'), (IA), (IA'), (IB), (IB'), (IC) or (IC')). Advantageously, the presently disclosed compounds have increased bioavailability relative to the alvocidib parent compound, and thus certain embodiments are directed to the foregoing pharmaceutical compositions formulated for oral delivery. Any of the carriers and/or excipients known in the art for oral formulation may be used in these embodiments, in addition to other carriers and/or excipients derivable by one of ordinary skill in the art.

For the purposes of administration, the compounds of the present invention may be administered as a raw chemical or may be formulated as pharmaceutical compositions. Embodiments of the pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, typically in an amount sufficient to treat a disease associated with overexpression of a cyclin-dependent kinase (CDK), and preferably with acceptable toxicity to the patient. Bioavailability of compounds of structure (I) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of embodiments of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of some embodiments of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of some embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of certain embodiments of the invention intended for either parenteral or oral administration should contain an amount of a compound of the invention such that a suitable dosage will be obtained.

In some embodiments, the pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of various embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

Embodiments of the pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of some embodiments of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of other embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In some embodiments, the concentration of the compound of structure (I) provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) provided in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

It will also be appreciated by those skilled in the art that, in the processes for preparing compounds of structure (I) described herein, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Compounds of structure (I) can be prepared by addition of a phosphate group to one of the three free hydroxyls of alvocidib. The alvocidib parent compound (and salts and solvates thereof) can be purchased from commercial sources or prepared according to methods known in the art, for example as described in U.S. Pat. Nos. 6,136,981; 6,225,473; 6,406,912; 6,576,647; and 6,821,990; the full disclosures of which are herein incorporated by reference in their entireties.

The following General Reaction Scheme illustrates a method of making compounds of this invention, i.e., compound of structure (I):

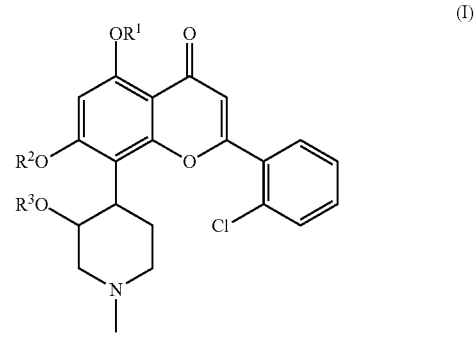

or a stereoisomer, tautomer or pharmaceutically acceptable salt thereof, wherein $R^1$, $R^2$ and $R^3$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

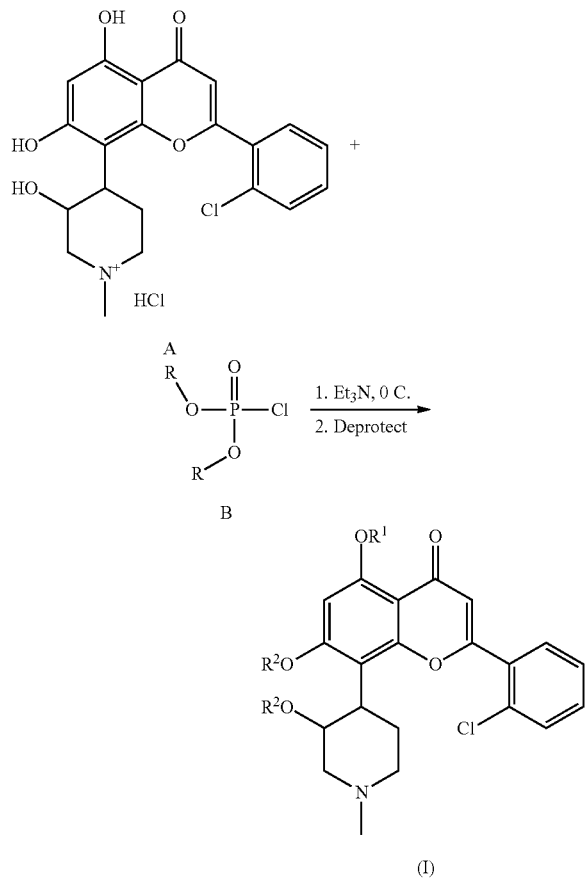

As shown in General Reaction Scheme 1, alvocidib HCl salt A is first reacted with an appropriately protected chlorophosphate (i.e., B, wherein R is a protecting group, such as ethyl). Deprotection then provides the desired compound of structure (I). It will be apparent to one of ordinary skill in the art that compounds of structure (I) having a single phosphate at any one of the three hydroxyl groups of alvocidib can be prepared according to the above scheme, and the desired regioisomer separated by usual techniques, such as chromatography. Protecting group strategies for optimizing the yield of the desired regioisomer will also be apparent to one of ordinary skill in the art.

Methods

In various embodiments, the invention provides a method for treating a disease in a mammal in need thereof by administration of a compound of structure (I), or a pharmaceutical composition comprising the same, to the mammal. In some specific embodiments, the method is for treating a disease associated with overexpression of a cyclin-dependent kinase (CDK) in a mammal in need thereof, the method comprising administering a therapeutically effective amount of any of the foregoing compounds of structure (I), or a pharmaceutical composition comprising the same, to the mammal.

In some more embodiments, the disease is cancer, for example a hematologic cancer. In some of these embodiments, the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma. In other embodiments, the hematological cancer is acute myelogenous leukemia (AML). In other different embodiments, the hematologic cancer is chronic lymphocytic leukemia (CLL). In still more different embodiments, the hematologic cancer is myelodysplasic syndrome (MDS).

In some other specific embodiments of the foregoing methods, the method comprises orally administering the compound of structure (I), or the pharmaceutical composition comprising the same, to the mammal.

In addition to the above exemplary diseases, a wide variety of cancers, including solid tumors and leukemias (e.g., acute myeloid leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

The compounds of the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. Due to intersubject variability in compound pharmacokinetics, individualization of dosing regimen is provided in certain embodiments. Dosing for a compound of the invention may be found by routine experimentation in light of the instant disclosure and/or can be derived by one of ordinary skill in the art.

EXAMPLES

Example 1

Preparation of Representative Phosphate Prodrug (IB')

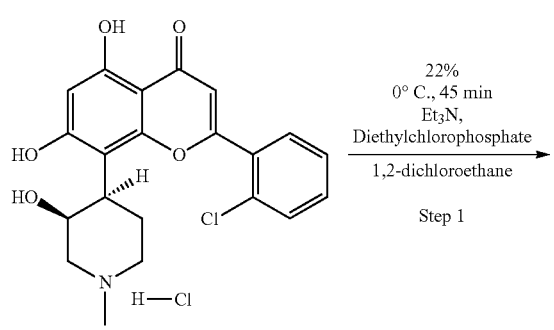

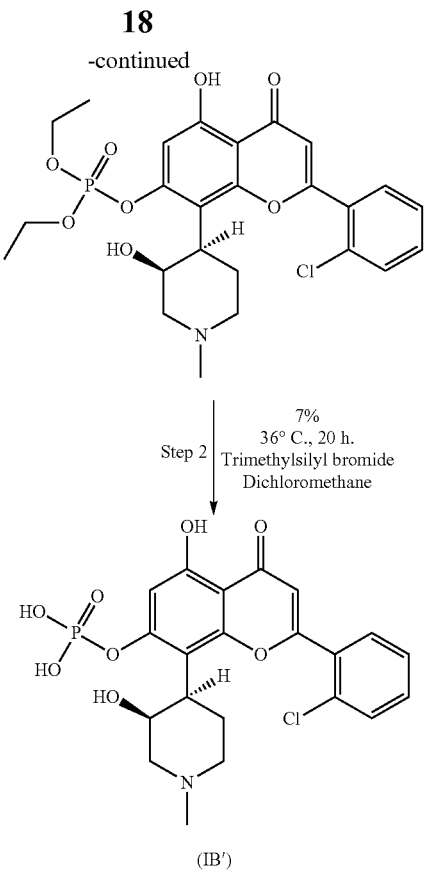

2-(2-chlorophenyl)-5-hydroxy-8-(3-hydroxy-1-methylpiperidin-4-yl)-4-oxo-4H-chromen-7-yl diethyl phosphate A suspension of alvocidib HCl (2 g, 4.56 mmol, 1 eq.) in 1,2-dichloroethane (40 mL) was cooled to 0° C. To this solution, triethylamine (1.9 mL, 13.7 mmol, 3 eq.) followed by diethylchlorophosphate (0.78 g, 4.56 mmol, 1 eq.) were added. The reaction mixture was stirred at 0° C. for 30-45 min. The reaction mixture was then poured onto ice and extracted with dichloromethane (3×25 mL). The combined organic layers were dried over anhydrous $Na_2SO_4$ and concentrated to get a crude residue. The crude residue was purified by flash column chromatography using 10-15% methanol in dichloromethane to afford 2-(2-chlorophenyl)-5-hydroxy-8-(3-hydroxy-1-methylpiperidin-4-yl)-4-oxo-4H-chromen-7-yl diethyl phosphate (550 mg, 1.02 mmol; 22%).

LCMS: Column: XBridge C8 (50×4.6 mm×3.5 μm); Mobile phase: A: 10 mM $NH_4CO_3$ in $H_2O$; B: ACN; RT: 5.97; Purity: (Max: 67.63); M+H: 538.0.

2-(2-chlorophenyl)-5-hydroxy-8-(3-hydroxy-1-methylpiperidin-4-yl)-4-oxo-4H-chromen-7-yl dihydrogen phosphate (IB')

To a solution of 2-(2-chlorophenyl)-5-hydroxy-8-(3-hydroxy-1-methylpiperidin-4-yl)-4-oxo-4H-chromen-7-yl diethyl phosphate (0.55 g, 1.02 mmol, 1 eq.) in dichloromethane (4 mL) at 0° C., trimethylsilylbromide (2.0 mL, 15.1 mmol, 15 eq.) was added. The reaction mixture was then heated at 36° C. under sealed condition for 20 h. The reaction mixture was evaporated. The crude residue obtained was purified by preparative HPLC to afford 2-(2-chlorophenyl)-5-hydroxy-8-(3-hydroxy-1-methylpiperidin-4-yl)-4-oxo-4H-chromen-7-yl dihydrogen phosphate (35 mg; 0.073 mmol; 7%).

LCMS: Column: XBridge C8 (50×4.6 mm×3.5 μm); Mobile phase: A: 10 mM NH$_4$CO$_3$ in H$_2$O; B: ACN; RT: 3.11; Purity: (Max: 93.56); M+H: 482.0.

HPLC: Column: XBridge C8 (50×4.6 mm×3.5 μm); Mobile phase: A: 0.1% TFA in H$_2$O; B: ACN; RT: 2.55; Purity: (Max: 96.39; 254 nm: 96.57).

1HNMR (DMSO-d$_6$-D$_2$O exchange): δ 7.84 (d, J=7.20 Hz, 1H), 7.71-7.70 (m, 1H), 7.65-7.62 (m, 1H), 7.59-7.55 (m, 1H), 7.07 (s, 1H), 6.62 (s, 1H), 4.12 (s, 1H), 3.60-3.54 (m, 1H), 3.30-3.26 (m, 3H), 3.13-3.11 (m, 2H), 2.71 (s, 3H), 1.83-1.80 (m, 1H).

Example 2

Pharmacokinetic Profile of Alvocidib Prodrugs

The following compounds were prepared and their pharmacokinetic profile determined and compared to the pharmacokinetic profile of compound (IB') as described below.

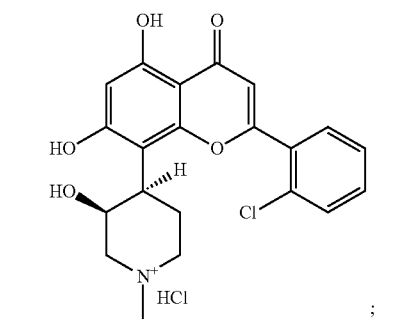
A

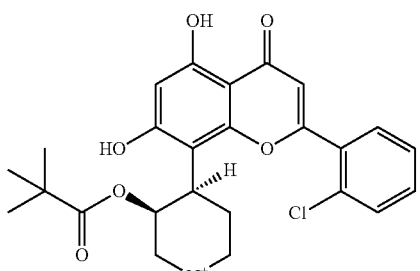
E and

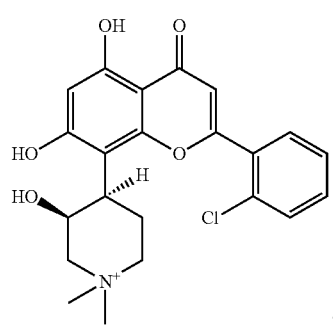 [SMILES: CN1CC[C@H](c2c(O)cc(O)c3c(=O)cc(-c4ccccc4Cl)oc23)[C@H](O)C1]
F

Compounds were prepared and administered to CD-1 mice intravenously (IV) or orally (PO) as summarized in Table 1. The plasma concentration of the alvocidib parent compound was determined at various time intervals (Table 2) and the pharmacokinetic parameters calculated (Table 3). Compounds E and F did not convert to alvocidib in vivo (i.e., no alvocidib was detected in plasma samples of mice treated with these compounds), and their pharmacokinetic parameters were not further investigated. As can be seen in Table 3, the bioavailability of compound (IB') is superior that of the parent alvocidib compound (A) and the two diphosphate compounds (C and D).

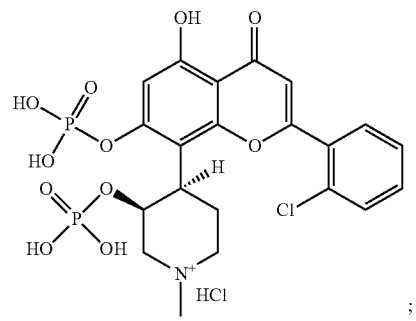
C

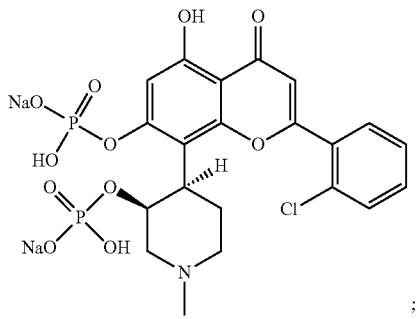
D

TABLE 1

| Design of Pharmacokinetic Profiling Experiments | | |
|---|---|---|
| | IV | PO |
| Dose (mg/kg) | 1 | 10 |
| Dosing volume (ml/kg) | 2 | 10 |
| Formulation Conc (mg/ml) | 0.5 | 1 |
| Formulation Detalis | | |
| IV Formulation | N-methyl pyrollidone:Ethanol:PEG200:NS (2:10:30:58) | |
| PO Formulation | Tween80:Ethanol:PEG400:water (2:10:30:58) | |
| Type of PK Planed | | |
| Species | Mouse | |
| Strain | ICR-CD1 | |
| Sex | Male | |
| Age/Body weight: | ~7-8 weeks/25-30 g | |
| Groups | IV: 1 gr; PO: 1 gr | |
| No of animals/group | 3/3 | |
| IV Dosing | Tail vein | |
| PO Dosing | oral gavage | |
| Sample Type | Plasma | |
| Blood collection | Saphenous vein | |
| Anticoagulant used | 0.2% K2 EDTA | |

TABLE 2

Plasma Concentration of Alvocidib
Alvocidib Plasma Concentrations (ng/ml)

| Time (hr) | A IV | A PO | C IV | C PO | D IV | D PO | (IB') IV | (IB') PO |
|---|---|---|---|---|---|---|---|---|
| 0.083 | 427.9 ± 26.5 | — | 30.1 ± 6.5 | — | 9.9 ± 8.0 | — | 366.8 ± 9.9 | — |
| 0.25 | 335.7 ± 641 | 1491 ± 211.0 | 53.4 ± 11.0 | 7.5 ± 4.2 | 31.4 ± 17.0 | 5.2 ± 4.7 | 265.1 ± 36.4 | 1868.7 ± 51.1 |
| 0.5 | 263.9 ± 48.2 | 1167.2 ± 186.0 | 62.1 ± 2.3 | 17.9 ± 1.0 | 43.8 ± 11.0 | 14.4 ± 1.8 | 183.6 ± 12.5 | 1880.5 ± 119.1 |
| 1.0 | 136.4 ± 41.9 | 675.5 ± 139.7 | 33.2 ± 15.1 | 28.5 ± 2.3 | 45.3 ± 7.2 | 39.3 ± 1.9 | 105.0 ± 17.8 | 1338.5 ± 188.8 |
| 2.0 | 52.5 ± 8.1 | 333.7 ± 94.5 | 19.8 ± 5.34 | 46.0 ± 3.8 | 17.0 ± 5.4 | 59.5 ± 5.9 | 40.2 ± 1.9 | 740.5 ± 147.4 |
| 4.0 | 28.9 ± 6.3 | 304.8 ± 29.5 | 13.5 ± 2.0 | 36.8 ± 1.7 | 9.4 ± 0.7 | 55.5 ± 3.6 | 16.8 ± 1.1 | 388.3 ± 35.7 |
| 6.0 | 13.5 ± 3.3 | 341.3 ± 53.3 | 5.9 ± 0.4 | 100 ± 4.5 | 4.4 ± 0.2 | 108.3 ± 1.4 | 7.22 ± 0.3 | 470.7 ± 18.4 |
| 8.0 | 6.7 ± 0.4 | 241.9 ± 24.9 | 3.6 ± 0.6 | 76.8 ± 3.3 | 2.2 ± 1.6 | 93.1 ± 3.7 | 2.9 ± 0.4 | 252.5 ± 31.0 |
| 24.0 | n.e. | 36.7 ± 11.1 | n.e. | 2.0 ± 0.3 | n.e. | n.e. | n.e. | 21.7 ± 17.5 |

Note:
Results are expressed in Mean ± SD, n = 3animals/group
n.e. = not evaluated

TABLE 3

Pharmacokinetic Profiles
Mice PK summary Table (Dose: IV-1 mg/kg & PO-10 mg/kg)

| PK Parameters | A IV | A PO | C IV | C PO | D IV | D PO | (IB') IV | (IB') PO |
|---|---|---|---|---|---|---|---|---|
| $C_{max}$ (ng/mL) | — | 1492.0 ± 211.0 | — | 100.1 ± 4.5 | — | 108.3 ± 1.4 | — | 1922.7 ± 72.1 |
| $T_{max}$ (h) | — | 0.25 ± 0.0 | — | 6.0 ± 0.1 | — | 6.0 ± 0.1 | — | 0.33 ± 0.14 |
| $AUC_{Last}$ (ng * h/mL) | 498.0 ± 46.0 | 5034.1 ± 145.6 | 132.8 ± 14.8 | 776.6 ± 32.8 | 109.0 ± 12.0 | 545.8 ± 11.9 | 363.6 ± 18.0 | 6619.6 ± 631.7 |
| $AUC_{0-\infty}$ (ng * h/mL) | 517.0 ± 47.0 | 5341.1 ± 274.2 | 144.6 ± 13.4 | 785.6 ± 33.5 | 114.3 ± 7.0 | — | 370.2 ± 19.0 | — |
| Clearance (L/h/Kg) | 1.9 ± 0.2 | — | 7.0 ± 0.7 | — | 8.8 ± 0.5 | — | 2.7 ± 0.14 | — |
| Vd (L/Kg) | 5.5 ± 1.2 | — | 22.0 ± 5.1 | — | 22.0 ± 13.1 | — | 6.1 ± 0.0 | — |
| $Vd_{SS}$ (L/Kg) | 3.8 ± 0.6 | — | 21.6 ± 4.4 | — | 23.5 ± 7.4 | — | 4.2 ± 0.1 | — |
| Half life (h) | 2.0 ± 0.4 | 5.7 ± 0.7 | 2.2 ± 0.5 | 3.1 ± 0.1 | 1.72 ± 0.9 | — | 1.57 ± 0.08 | 4.4 ± 1.3 |
| Bioavail. (% F) | | 102 ± 11.7 | | 59.0 ± 8.0 | | 50.5 ± 4.7 | — | 182.3 ± 20.0 |

Note: Results are Expressed in Mean±SD, N=3Animals/Groupexample 3

Kinetic Solubility Profiles

The aqueous kinetic solubility of compound IB was determined across a broad pH range (i.e. pH 2.2-pH 8.7) and compared to the aqueous kinetic solubility of alvocidib for the same pH range. The solubility of compound IB' was found to be in excess of 1 mg/mL at the lowest pH tested (pH 2.2), rising to above 5 mg/mL at pH 6.8 and pH 8.7. By comparison, the solubility of alvocidib is above 1 mg/mL at pH 2.2 and pH 4.5 but drops to 0.02 mg/mL at pH 6.8 and pH 8.7.

TABLE 4

Kinetic Solubility Profiles

| Compound | Concentration tested (mg/mL) | Solubility (mg/mL) pH 2.2 | pH 4.5 | pH 6.8 | pH 8.7 |
|---|---|---|---|---|---|
| Alvocidib | 1 | 1.05 | 0.95 | 0.02 | 0.00 |
|  | 5 | 4.82 | 1.99 | 0.02 | 0.02 |
|  | 10 | 4.38 | 1.25 | 0.02 | 0.02 |
| Compound IB' | 1 | 1.07 | 1.10 | 1.09 | 1.09 |
|  | 5 | 1.90 | 2.33 | 5.56 | 5.65 |
|  | 10 | 1.52 | 1.81 | 9.48 | 9.31 |

Example 4

Plasma Stability Profiles

The plasma stability of compound IB' was determined using plasma from four species. Results for mouse, rat, dog and human are shown in Tables 5, 6, 7 and 8 respectively. Alvocidib and flumazenil were used as controls. In mouse, rat and human plasma, compound IB' maintained 100% stability after 5 hour incubation. In dog plasma, approximately 90% of compound IB' remained after 5 hours. By comparison, alvocidib maintained 100% stability across all four species after 5 hours, and flumazenil was unstable in mouse and rat plasma.

TABLE 5

Mouse Plasma Stability Profiles

| Compound | 0 hours | 0.5 hours | 1 hour | 2 hours | 3 hours | 4 hours | 5 hours |
|---|---|---|---|---|---|---|---|
| | | | | % Remaining | | | |
| Flumazenil | 100.00 | 29.96 | 10.21 | 1.56 | 0.39 | 0.20 | 0.07 |
| Alvocidib | 100.00 | 93.58 | 103.12 | 97.19 | 117.38 | 115.72 | 111.28 |
| Compound IB' | 100.00 | 88.48 | 89.83 | 97.71 | 99.61 | 100.46 | 100.20 |

TABLE 6

Rat Plasma Stability Profiles

| Compound | 0 hours | 0.5 hours | 1 hour | 2 hours | 3 hours | 4 hours | 5 hours |
|---|---|---|---|---|---|---|---|
| | | | | % Remaining | | | |
| Flumazenil | 100.00 | 42.23 | 16.13 | 1.69 | 0.23 | 0.00 | 0.00 |
| Alvocidib | 100.00 | 93.12 | 90.20 | 99.31 | 98.69 | 92.57 | 117.71 |
| Compound IB' | 100.00 | 97.39 | 94.60 | 100.04 | 107.48 | 100.20 | 99.78 |

TABLE 7

Dog Plasma Stability Profiles

| Compound | 0 hours | 0.5 hours | 1 hour | 2 hours | 3 hours | 4 hours | 5 hours |
|---|---|---|---|---|---|---|---|
| | | | | % Remaining | | | |
| Flumazenil | 100.00 | 91.80 | 92.00 | 100.99 | 115.10 | 99.44 | 100.53 |
| Alvocidib | 100.00 | 96.41 | 89.16 | 105.76 | 105.84 | 97.65 | 100.40 |
| Compound IB' | 100.00 | 83.66 | 94.53 | 112.61 | 99.16 | 93.91 | 90.24 |

TABLE 8

Human Plasma Stability Profiles

| Compound | 0 hours | 0.5 hours | 1 hour | 2 hours | 3 hours | 4 hours | 5 hours |
|---|---|---|---|---|---|---|---|
| | | | | % Remaining | | | |
| Flumazenil | 100.00 | 96.56 | 90.83 | 92.41 | 117.98 | 95.32 | 94.63 |
| Alvocidib | 100.00 | 92.61 | 93.54 | 93.29 | 111.62 | 100.25 | 104.65 |
| Compound IB' | 100.00 | 96.32 | 88.01 | 104.22 | 102.59 | 94.36 | 100.26 |

Example 5

Pharmacokinetics in Sprague Dawley Rats

The plasma concentrations of alvocidib produced by oral and intravenous (IV) administration of compound IB' and of absorbed compound IB' itself, were determined in male Sprague Dawley (SD) rats (see FIG. 1). Plasma samples were taken at 8 time-points (IV) or 7 time points (oral) over a 24 hour period following a single dose of compound IB' (3 animals per group). The calculated pharmacokinetic parameters are shown in Table 9 and Table 10. Both IV and oral administration of compound IB' led to significant exposure of alvocidib. Administered intravenously, compound IB' (1 mg/kg) was metabolized to alvocidib with a $C_0$ of 270.3 ng/mL which was eliminated with a half-life of 1.6 hours. Administered orally, compound IB' (10 mg/kg) was metabolized to alvocidib with a $C_{max}$ of 178.6 ng/mL and a $T_{max}$ of 2.92 hours, which was eliminated with a half-life of 4.4 hours. The bioavailability of alvocidib (99.03%) was calculated from the ratio of the area under the curve (AUC) for alvocidib produced from oral and IV administration of compound IB'. The plasma samples were also analyzed for the presence of compound IB'. The plasma concentrations of compound IB' in SD rats are also shown in FIG. 1 and Table 11. For both IV and oral administration in SD rats, plasma levels of compound IB' dropped below quantitative levels at 2 hours post dosing.

TABLE 9

Pharmacokinetic Parameters for Alvocidib Following Intravenous Administration of Compound IB' in Sprague Dawley Rats

| Parameter | Value | SD |
|---|---|---|
| $C_0$ (ng/mL) | 270.3 | 48.6 |
| $AUC_{in}$ (hr · ng/mL) | 135.6 | 21.1 |
| $AUC_{0-t}$ (hr · ng/mL) | 129.9 | 22.8 |
| $AUC_{in}/AUC_{0-t}$ (%) | 104.6 | 2.3 |
| $V_d$ (L/kg) | 17.50 | 1.93 |
| $CL_p$ (L/hr/kg) | 7.5 | 1.1 |
| $V_{d,ss}$ (L/kg) | 17.71 | 10.08 |
| $MRT_{in}$ (hr) | 2.5 | 1.8 |
| $t_{1/2}$ (hr) | 1.6 | 0.4 |

TABLE 10

Pharmacokinetic Parameters for Alvocidib Following Oral Administration of Compound IB' in Sprague Dawley Rats

| Parameter | Value | SD |
|---|---|---|
| $C_{max}$ (ng/mL) | 178.6 | 47 |
| $T_{max}$ (hr) | 2.92 | 4.4 |
| $AUC_{in}$ (hr · ng/mL) | 1280.5 | 194 |
| $AUC_{0-t}$ (hr · ng/mL) | 1241.2 | 185 |
| $AUC_{in}/AUC_{0-t}$ (%) | 103.2 | 0.8 |
| Bioavailability (%) | 99.03 | 30.2 |
| $t_{1/2}$ (hr) | 4.40 | 0.5 |

TABLE 11

Plasma Concentrations of Compound IB following Intravenous or Oral Administration of Compound IB' in Sprague Dawley Rats

| Time (hr) | IV (ng/mL) | SD | PO (ng/mL) | SD |
|---|---|---|---|---|
| 0.083 | 429.6 | 144.0 | # | # |
| 0.25 | 82.0 | 6.6 | 30.0 | 9.7 |
| 0.50 | 24.6 | 4.2 | 20.4 | 6.6 |
| 1.00 | 9.3 | 2.8 | 9.3 | 0.4 |
| 2.00 | BQL | — | BQL | — |
| 4.00 | BQL | — | BQL | — |
| 6.00 | BQL | — | BQL | — |
| 8.00 | BQL | — | BQL | — |
| 24.00 | BQL | — | BQL | — |

\# not measured
BQL = below quantitation limit

Example 6

Maximum Tolerated Acute Dose in Mice

Figure 2A:
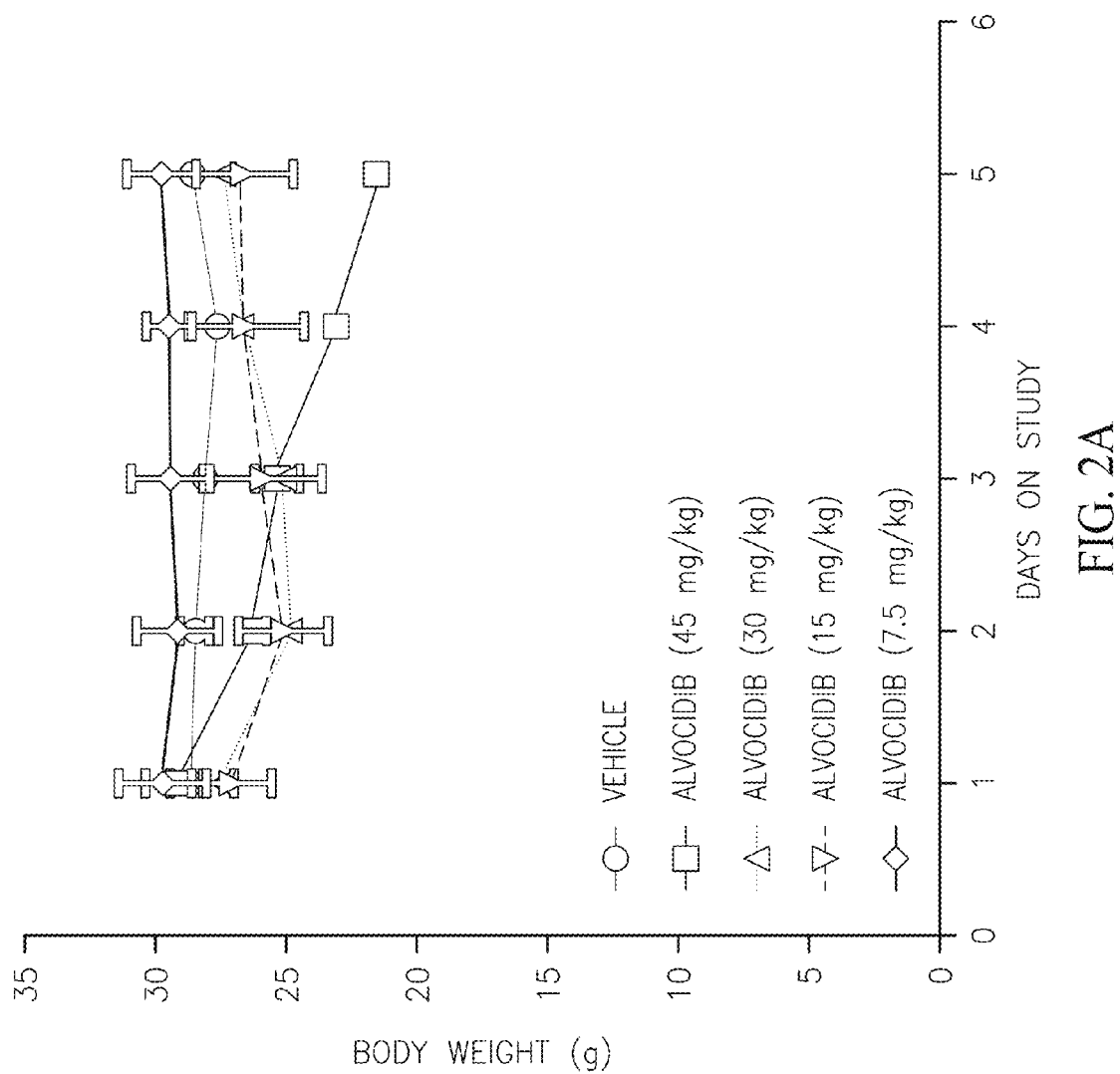
FIG. 2A-D depict the body weights of mice treated with a single dose (FIG. 2A-B orally, FIG. 2C-D intravenously) of alvocidib or compound IB.
Figure 2B:
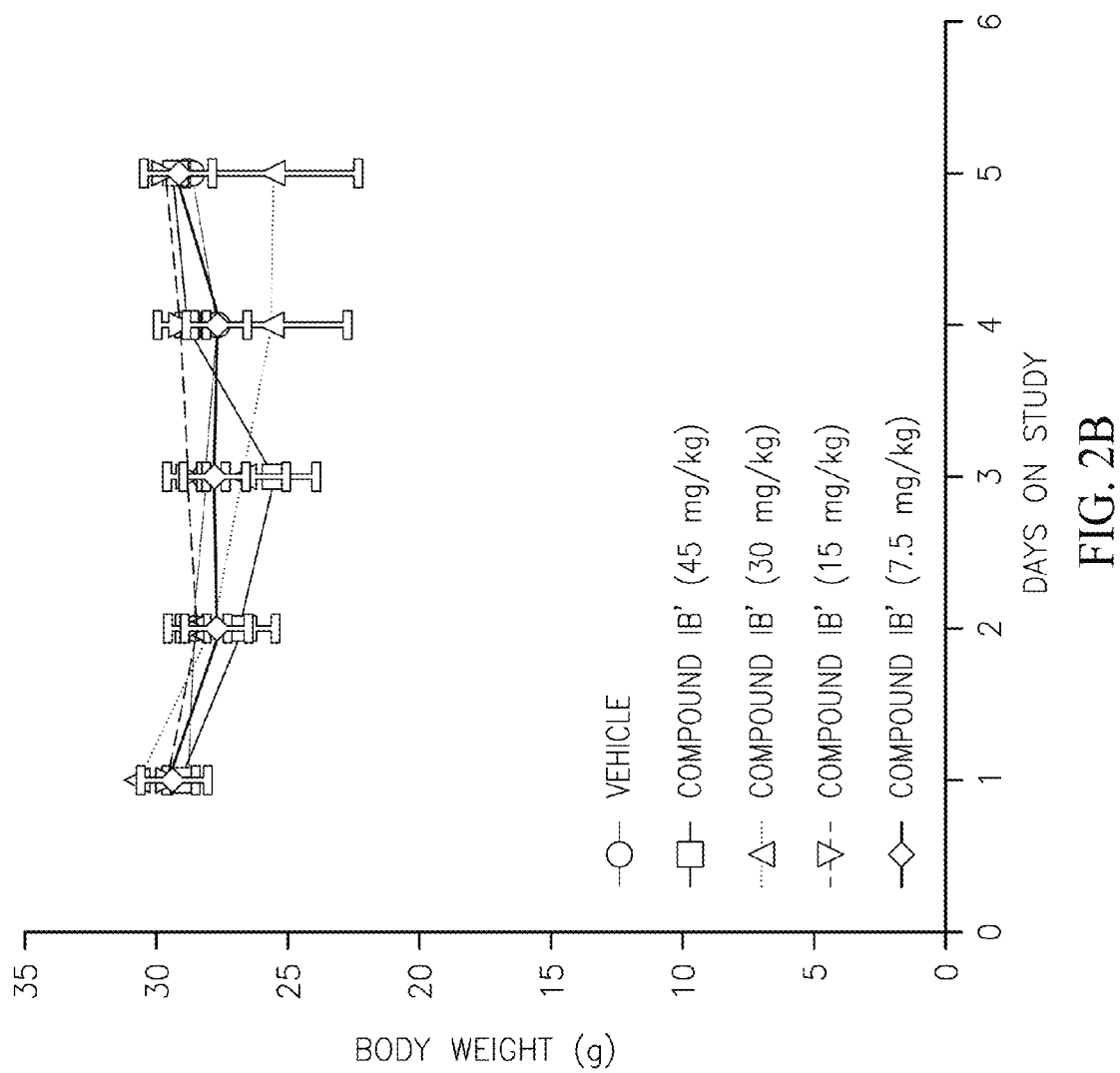
Figure 2C:
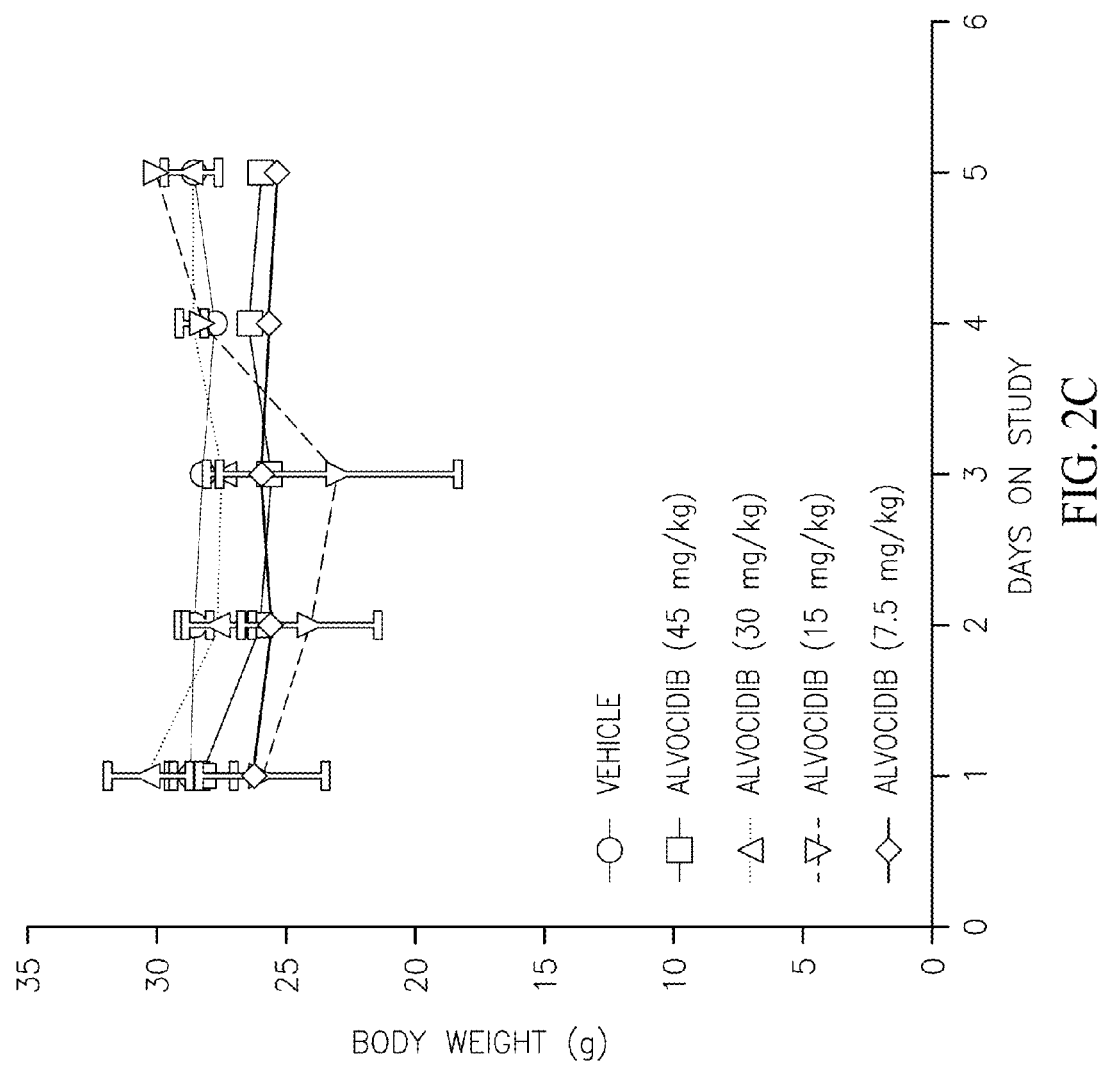
Figure 2D:
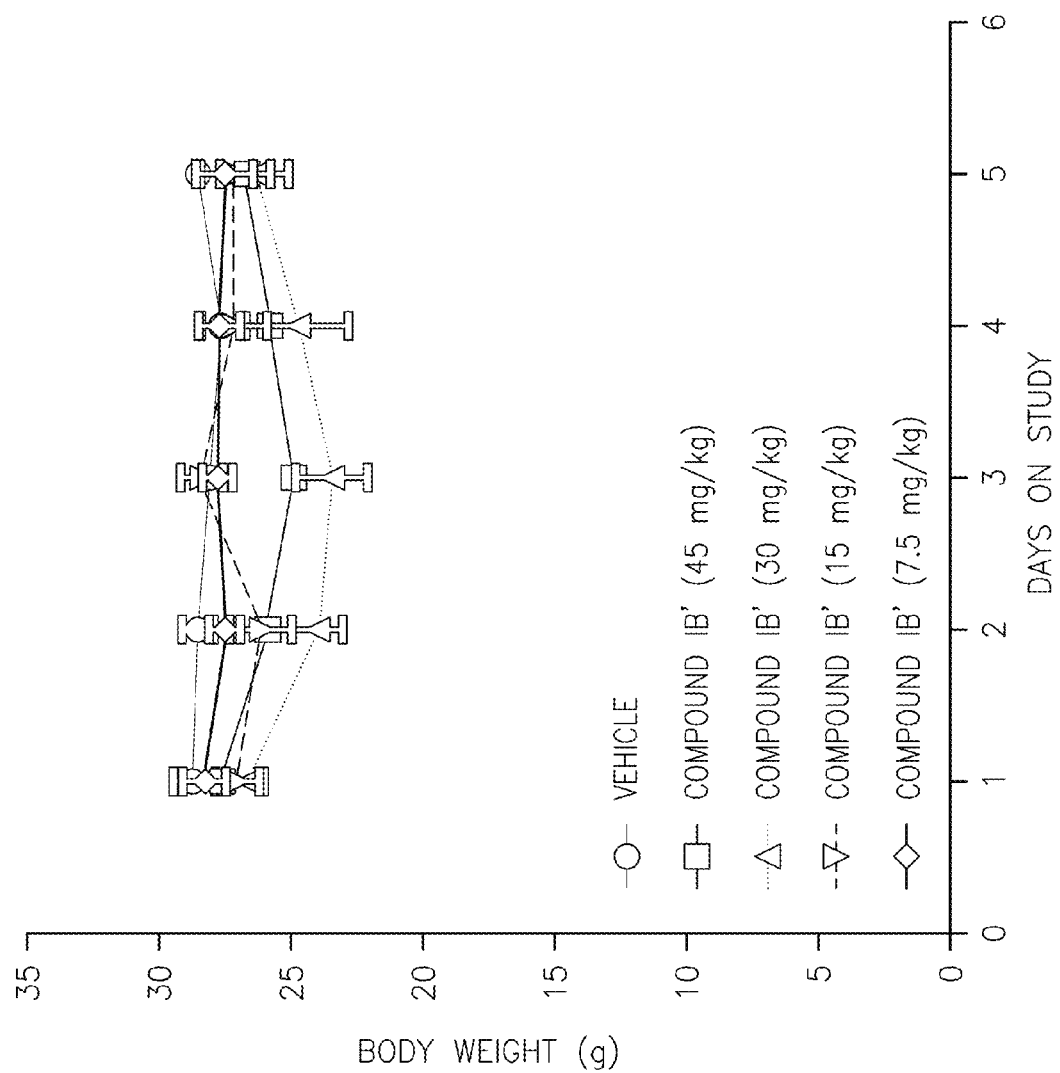

Acute (i.e. single dose) toxicology studies were performed in mice. Acute studies were performed in female SHO SCID mice using three animals per treatment group. Animals were treated with a single dose of compound IB' at 45, 30, 15, or 7.5 mg/kg. For comparison, additional animals were treated with alvocidib at the same dose levels. Body weight measurements following oral dosing (FIGS. 2A-B) and intravenous (IV) dosing (FIG. 2C-D) were used, along with mortality and clinical observations to determine the maximum tolerated acute dose ($MTD_{acute}$).

The results from the acute study determined that the $MTD_{acute}$ of compound IB', dosed orally, is 15 mg/kg. The $MTD_{acute}$ of compound IB', dosed intravenously, is 15 mg/kg. Body weight loss and increased lethargy were observed in animals dosed at 30 mg/kg and 45 mg/kg. In animals dosed orally at 45 mg/kg, one animal died on day two and one animal died on day three. In animals dosed orally at 30 mg/kg, one animal died on day four. In animals dosed intravenously at 45 mg/kg, two animals died on day two. In animals dosed intravenously at 30 mg/kg, one animal died on day three.

The acute $MTD_{acute}$ of alvocidib, when dosed orally, is 15 mg/kg. The $MTD_{acute}$ of alvocidib, dosed intravenously, is 7.5 mg/kg. Some body weight loss, increased lethargy, and animal deaths were observed in animals dosed with alvocidib at both the 30 and 45 mg/kg dose levels.

Body weight loss was observed in surviving animals at 45 mg/kg and 30 mg/kg oral dosing levels of compound IB', peaking at 17% in the 30 mg/kg group. Body weight loss in surviving animals dosed intravenously peaked at 12%.

No overt toxicity was observed in mice dosed orally or intravenously at 15 mg/kg or 7.5 mg/kg. Minor body weight loss peaking at 3.3% in the 15 mg/kg intravenous dosing group was attributed to normal body weight fluctuation in test animals.

Compound IB' is better tolerated ($MTD_{acute}$=15 mg/kg) in mice when dosed intravenously compared to alvocidib ($MTD_{acute}$=7.5 mg/kg).

Example 7

Maximum Tolerated Repeated Dose Schedule in Mice

Figure 3A:
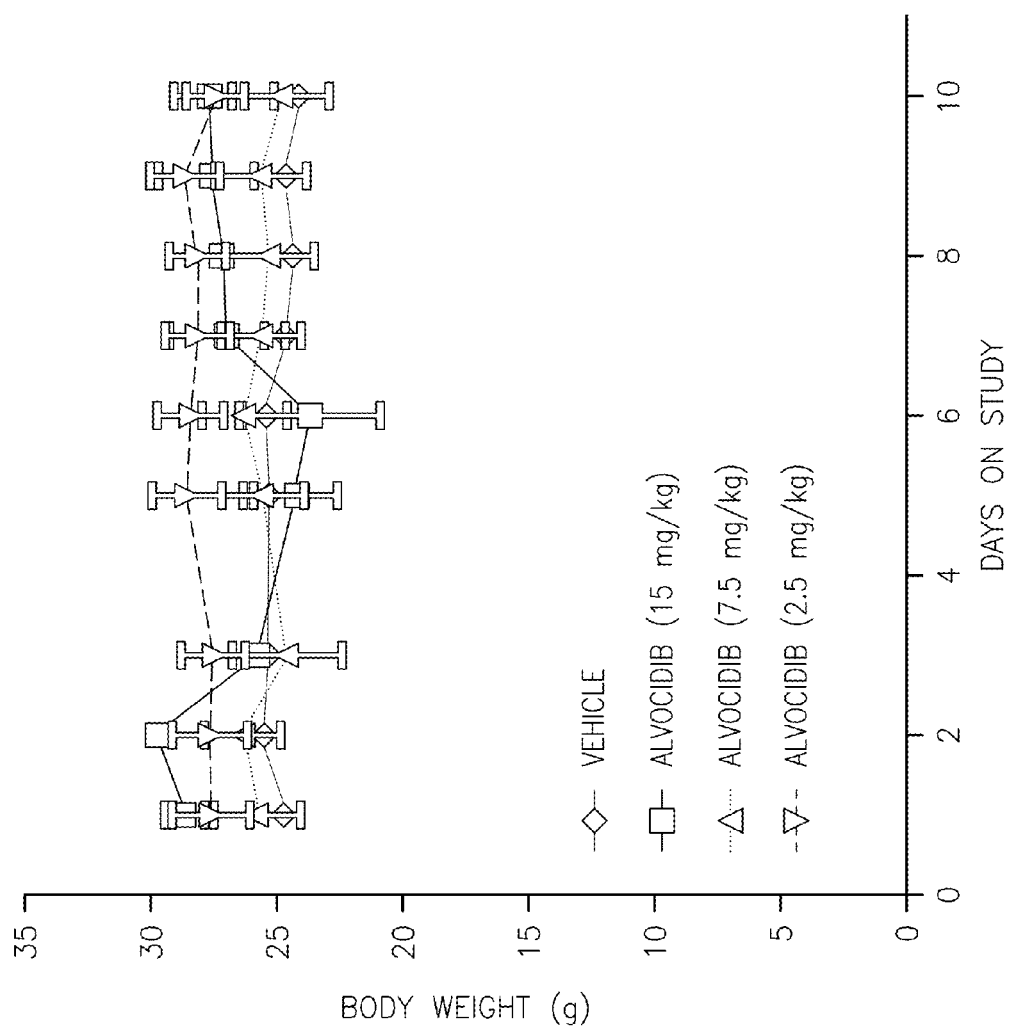
Figure 3B:
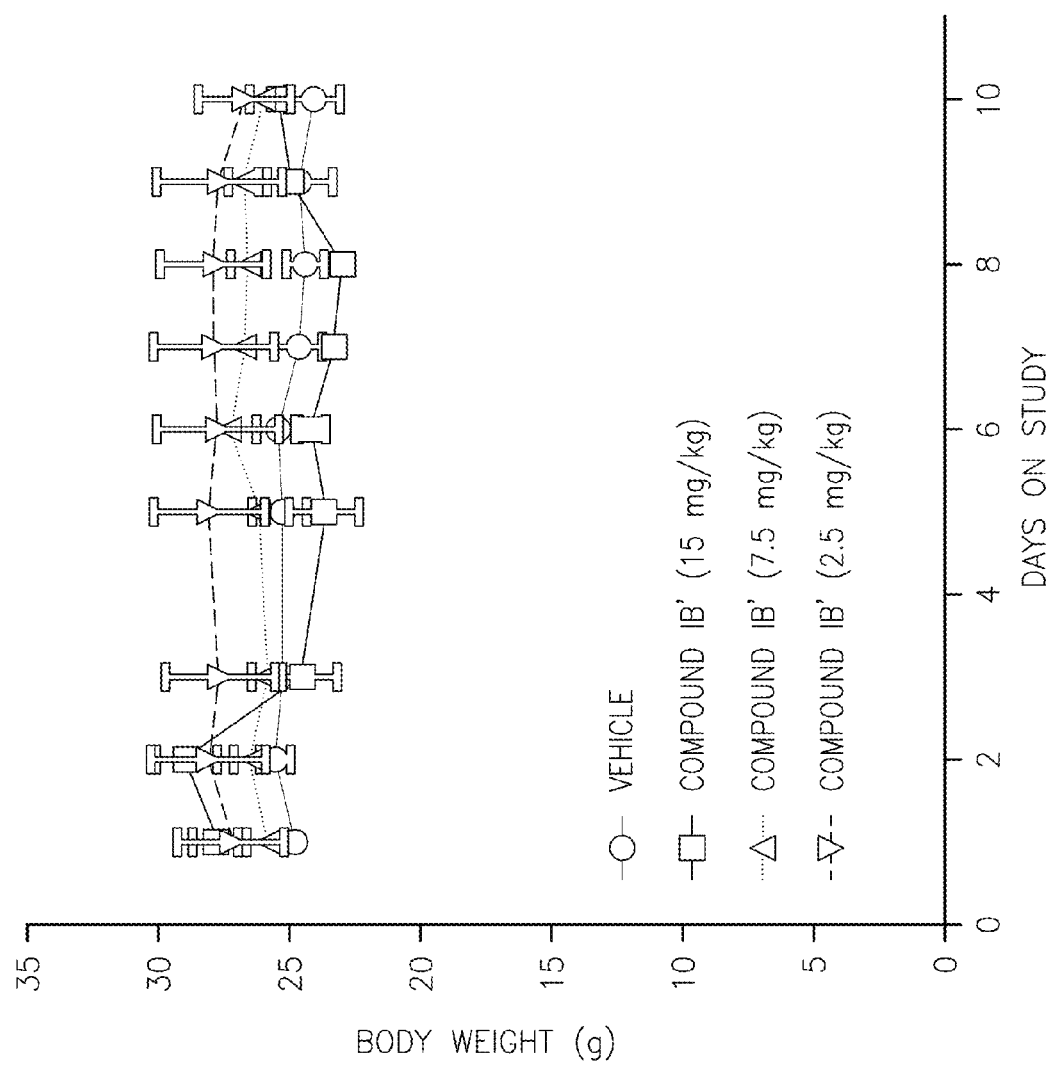
Figure 3C:
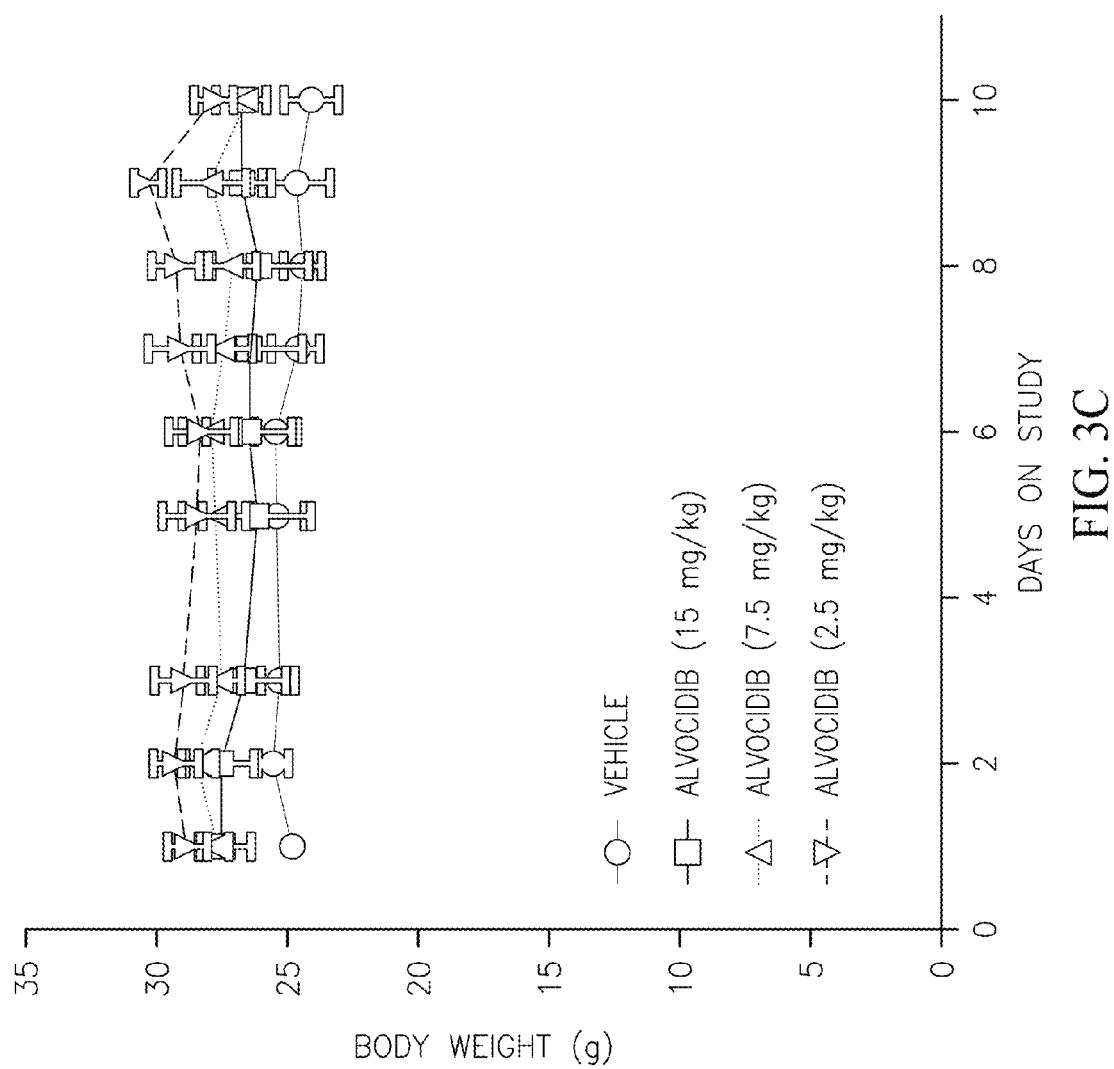

Repeat dose toxicology studies were performed in female SHO SCID mice using 3 animals per treatment group. Animals were treated with five daily doses of compound IB at 15, 7.5, or 2.5 mg/kg, and were observed for five additional days following the dosing regimen. For comparison, additional animals were treated with alvocidib at the same dose levels and the same dosing/observation schedule. Body weight measurements of animals treated by oral (see FIGS. 3A-B) and intravenous (see FIGS. 3C-D) dosing over the course of the 5-day repeat dosing period and subsequent 5-day observation period, along with mortality and clinical observations, were used to determine the maximum tolerated dosing schedule ($MTD_{repeat}$).

The results from the 5-day repeat-dose study determined that the $MTD_{repeat}$ of compound IB, dosed orally, is 7.5 mg/kg. The $MTD_{repeat}$ of compound IB', dosed intravenously, is 15 mg/kg. Body weight loss was observed in animals dosed orally at 15 mg/kg. In animals dosed orally at 15 mg/kg, one animal died on day 5, and one animal died on day 7.

For comparison, the $MTD_{repeat}$ determined for alvocidib, when dosed orally, was 7.5 mg/kg. The $MTD_{repeat}$ determined for alvocidib, when dosed intravenously, was 7.5 mg/kg. Lethargy, body weight loss, and deaths were observed at the 15 mg/kg dosing levels for both oral and intravenous dosing with alvocidib.

Body weight loss was observed in surviving animals at the 15 mg/kg oral dosing level with compound IB', which peaked at 12%. No overt toxicity was observed in animals dosed orally at 7.5 mg/kg or 2.5 mg/kg, or in animals dosed at any dose level attempted when administered intravenously.

Compound TB' is better tolerated ($MTD_{repeat}$=15 mg/kg) in mice when dosed intravenously compared to alvocidib ($MTD_{repeat}$=7.5 mg/kg).

Example 8

Maximum Tolerated Acute Dose in Rats

Acute (i.e. single dose) toxicology studies were performed in rats. Acute studies were performed in female Sprague Dawley rats using three animals per treatment group. Animals were treated with a single dose of compound IB' at 36, 18, 9, or 4.5 mg/kg. For comparison, additional animals were dosed with 18, 9, or 4.5 mg/kg alvocidib. Body weight measurements following oral dosing (see FIG. 4A), along with mortality, clinical observations, food consumption (see FIG. 4B), and complete blood counts (CBCs; see Table 12) were used to determine the maximum tolerated acute dose ($MTD_{acute}$).

The results from the acute study determined that the $MTD_{acute}$ of compound IB' in rats is 18 mg/kg. Diarrhea, body weight loss and increased lethargy were observed in animals dosed with compound IB at 36 mg/kg. At this dose level, one animal died on day three, one animal died on day four, and one animal died on day 5. Deaths were not observed in any other treatment group.

Figure 4A:
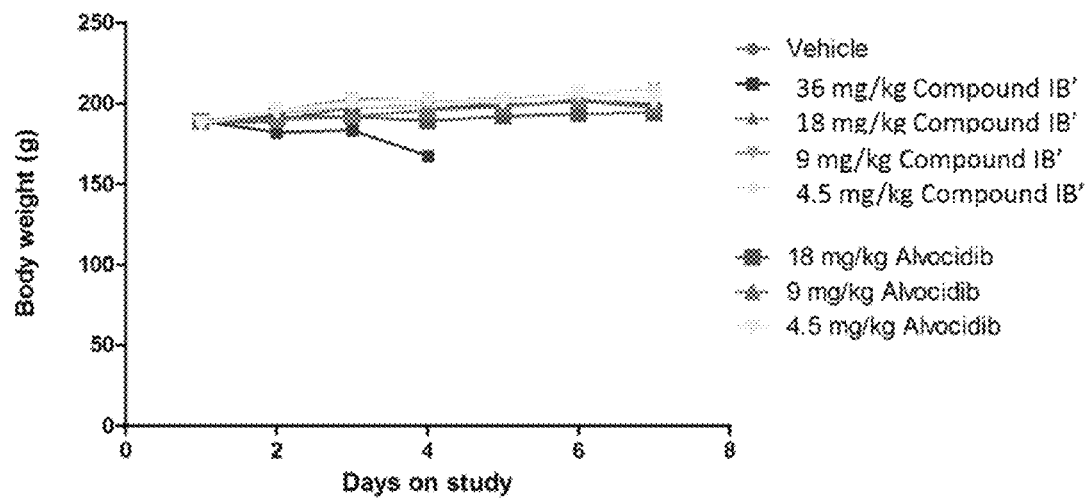
FIG. 4A-B show body weights and food consumption of rats treated with a single dose (orally) of alvocidib or compound IB.
Figure 4B:
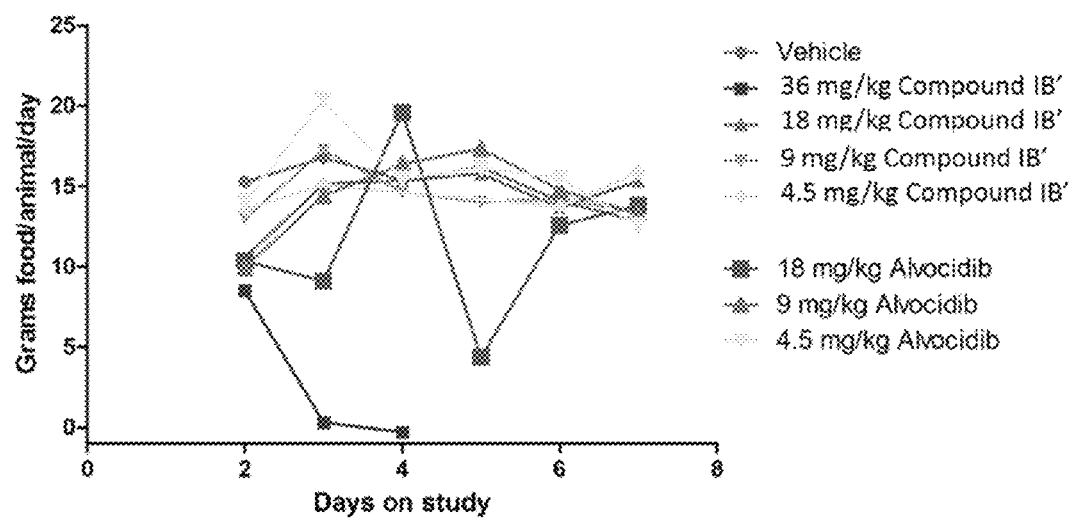

Body weight loss was observed in treated animals, preceding death, reaching 13.1% in animals treated at the 36 mg/kg dose level with compound IB' (see FIG. 4A). This body weight loss was accompanied by significant diarrhea, and increased lethargy in these animals. No overt toxicity, including body weight change or diarrhea, was observed in rats dosed at 18, 9, or 4.5 mg/kg with compound IB'. In comparison, animals dosed with 18 mg/kg alvocidib did show signs of diarrhea. In addition, abnormal food consumption patterns were observed with 18 mg/kg dosing of alvocidib that were not observed with the compound IB' treated animals at the same dosage level.

Abnormal CBCs were Observed in some animals (Table 12). Specifically, platelet counts were outside the normal range for the vehicle and 9 mg/kg dosage of compound IB', and 4.5 mg/kg alvocidib dose. No consistent dose-dependent trend was observed in the surviving, treated animals. Slightly reduced red and white blood cell counts were observed at the 18 mg/kg dose level for compound IB'. However, slightly elevated counts were also observed in some untreated animals as well. The high variability of these results was attributed to inter-animal variation, and not drug-dependent mechanisms. As animals treated with 36 mg/kg of compound IB' expired overnight, CBCs were not available.

Based on the data above, the rat oral $MTD_{acute}$ of compound IB' was found to distinguish its tolerability profile versus that of alvocidib as the no observable adverse effect level (NOAEL) was found to be 18 mg/kg for compound IB' and 9 mg/kg for alvocidib.

Example 9

Mouse Xenograft Efficacy Study

Figure 5A:
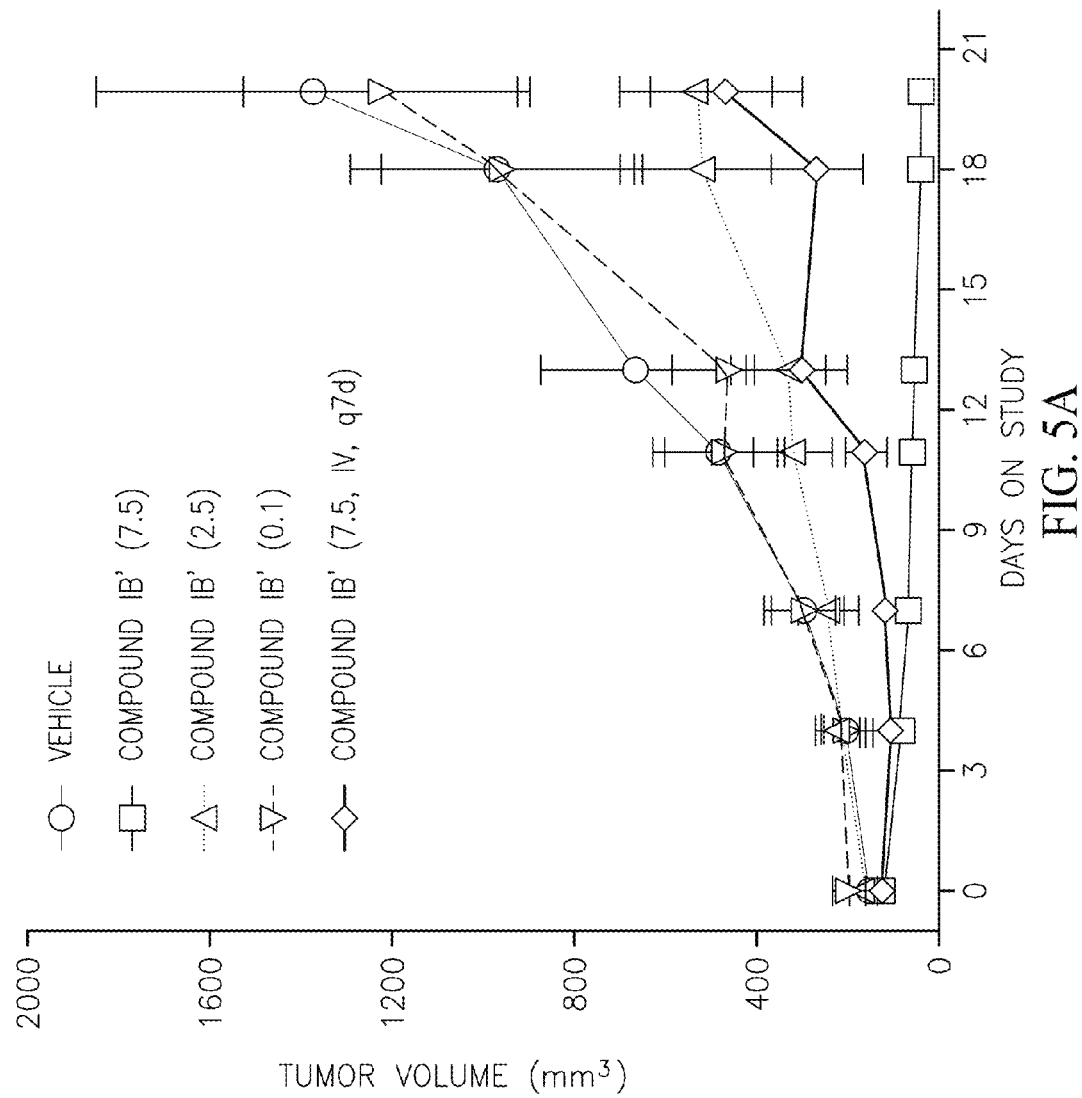
FIG. 5A-B show in vivo tumor volume and body weight after dosing with compound IB during a xenograft efficacy study.
Figure 5B:
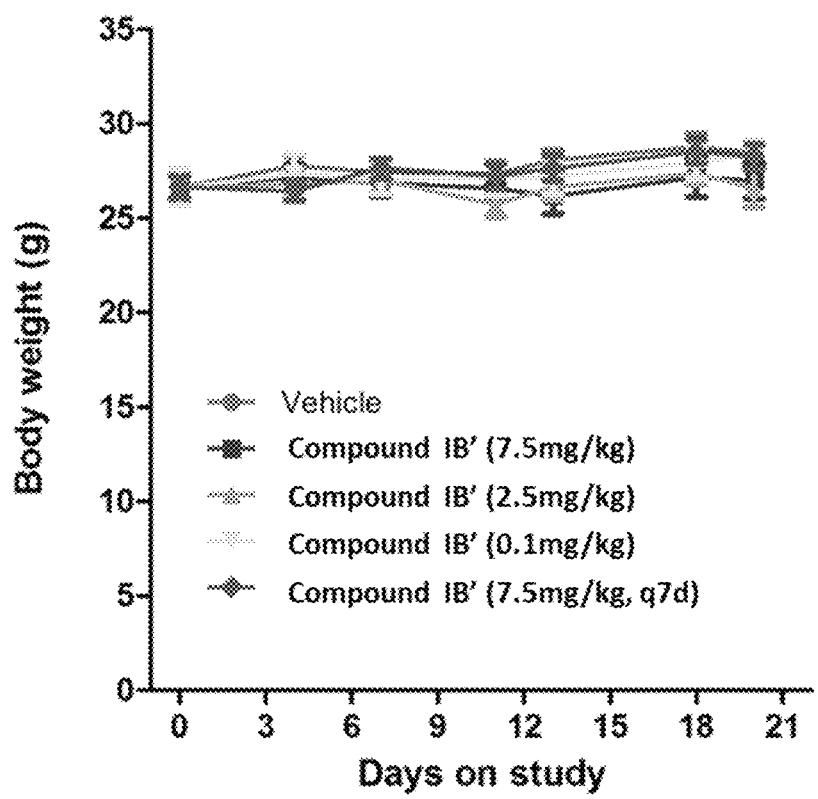

The in vivo activity of compound IB' was determined in a MV4-11 mouse xenograft model of acute myeloid leukemia (AML). Injection of $8 \times 10^6$ MV4-11 cells/mouse was followed by growth of tumors to approximately 100 mm$^3$. After tumors reached the appropriate size, mice were randomized into the following treatment groups: Vehicle, compound IB' (7.5 mg/kg, qdx5x3), compound (2.5 mg/kg, qdx5x3), compound IB' (0.1 mg/kg, qdx5x3) and compound IB (7.5 mg/kg, q7dx3). Vehicle and compound IB' were administered orally, except in the last arm of compound IB' (7.5 mg/kg, q7dx3), which was dosed intravenously. Treatment resulted in significant tumor growth inhibition (% TGI; see FIGS. 5A-B and Table 13).

TABLE 13

Tumor Growth Inhibition for Mouse Xenograft Efficacy Study

| Dosage of Compound IB' | Tumor Growth Inhibition (%) |
| --- | --- |
| Vehicle (i.e. no compound IB') | 0 |
| 7.5 mg/kg | 69 |
| 2..5 mg/kg | 12 |
| 7.5 mg/kg, q7dx3 | 74 |

Example 10

Mouse Xenograft Pharmacodynamic Study

Figure 6A:
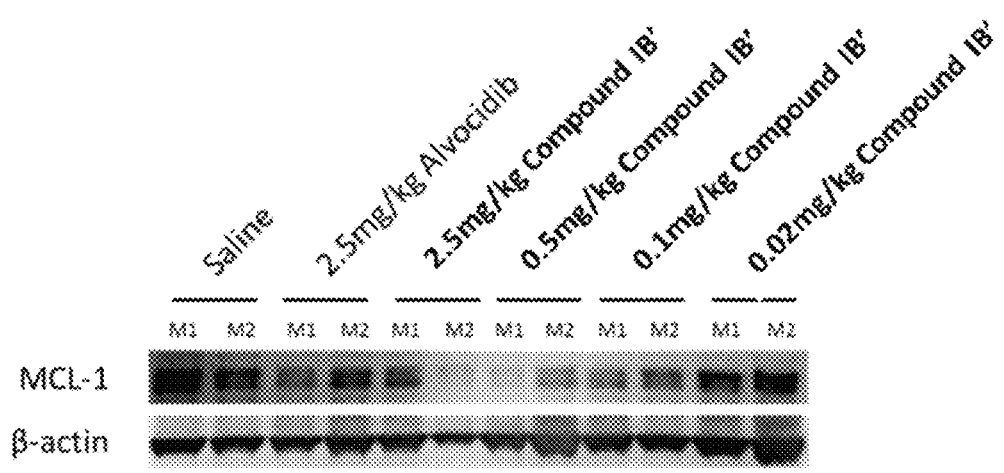
FIG. 6A-B depict reduction of MCL-1 protein expression following treatment with compound IB during a xenograft pharmacodynamic study.
Figure 6B:
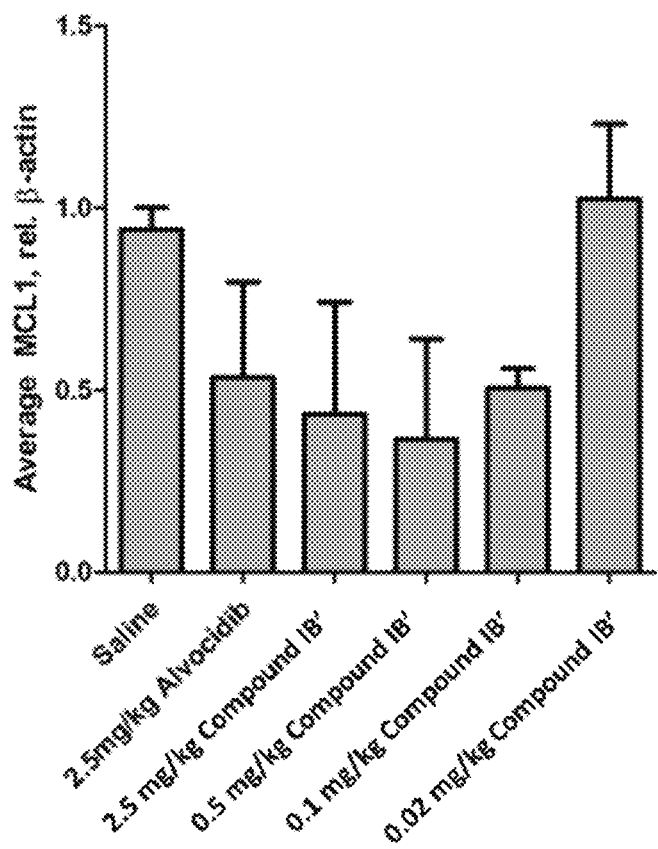

The in vivo pharmacodynamic activity of compound IB' was determined in a MV4-11 mouse xenograft model of AML (FIG. 6A-B), Injection of $8 \times 10^6$ cells/mouse was followed by growth of tumors to approximately 100 mm$^3$. After tumors reached an appropriate size, mice were randomized into the following treatment groups: Vehicle, compound (2.5 mg/kg), compound IB' (0.5 mg/kg), compound IB' (0.1 mg/kg), compound IB' (0.02 mg/kg). Mice were administered a single treatment dose and tumors were harvested 48 hours post-treatment. MCL-1 protein levels were assessed on harvested tumors using standard polyacrylamide gel electrophoresis and immunoblotting technique (FIG. 6A). Treatment resulted in reduction of MCL-1 protein expression (see FIG. 6B and Table 14 below).

TABLE 12

Blood Counts of Rats Treated With a Single Dose of Compound IB

| | RBC ($10^6/\mu L$) | MCV (fL) | HCT (%) | MCH (pg) | MCHC (g/dL) | RDWA (fL) | PLT ($10^3/\mu L$) | HGB (g/dL) | WBC ($10^3/\mu L$) |
| --- | --- | --- | --- | --- | --- | --- | --- | --- | --- |
| Vehicle | 7.8 | 53.1 | 41.5 | 19.5 | 36.8 | 15.7 | 34.3 | 174.3 | 15.2 |
| 36 mg/kg compound IB' | — | — | — | — | — | — | — | — | — |
| 18 mg/kg compound IB' | 5.9 | 53.5 | 31.2 | 19.6 | 36.6 | 15.7 | 33.9 | 201.3 | 11.4 |
| 9 mg/kg compound IB' | 8.0 | 53.3 | 42.7 | 19.5 | 36.6 | 15.9 | 35.0 | 112.7 | 15.6 |
| 4.5 mg/kg compound IB' | 9.1 | 54.8 | 49.9 | 19.7 | 35.9 | 16.2 | 37.1 | 319.3 | 17.9 |
| 18 mg/kg alvocidib | 8.8 | 53.8 | 47.3 | 19.3 | 35.9 | 16.1 | 36.1 | 376.0 | 16.9 |
| 9 mg/kg alvocidib | 8.7 | 54.0 | 47.1 | 19.3 | 35.7 | 16.2 | 36.3 | 334.7 | 16.8 |
| 4.5 mg/kg alvocidib | 8.3 | 52.7 | 43.6 | 18.7 | 35.4 | 16.0 | 34.7 | 147.0 | 15.4 |

TABLE 14

| Reduction of MCL-1 Protein Expression | |
|---|---|
| Dosage of Compound IB' | Reduction of MCL-1 Expression (%) |
| Vehicle (i.e. no compound IB') | 0.0 |
| 2.5 mg/kg | 54 |
| 0.5 mg/kg | 61 |
| 0.1 mg/kg | 46 |
| 0.02 mg/kg | 0.0 |

All of the U.S. patents, U.S. patent application publications, U.S. patent applications, foreign patents, foreign patent applications and non-patent publications referred to in this specification, including U.S. Provisional Patent Application Ser. No. 62/163,188, filed May 18, 2015, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (I):

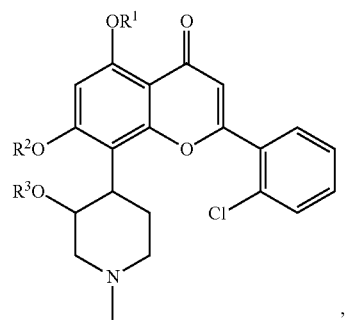

or a stereoisomer, tautomer or pharmaceutically acceptable salt thereof, wherein:
i) $R^1$ is —P(=O)(OH)$_2$, and $R^2$ and $R^3$ are each H;
ii) $R^2$ is —P(=O)(OH)$_2$, and $R^1$ and $R^3$ are each H; or
iii) $R^3$ is —P(=O)(OH)$_2$, and $R^1$ and $R^2$ are each H.

2. The compound of claim 1, having the following structure (I'):

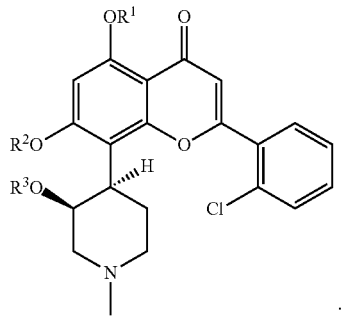

3. The compound of claim 1, having the following structure (IA):

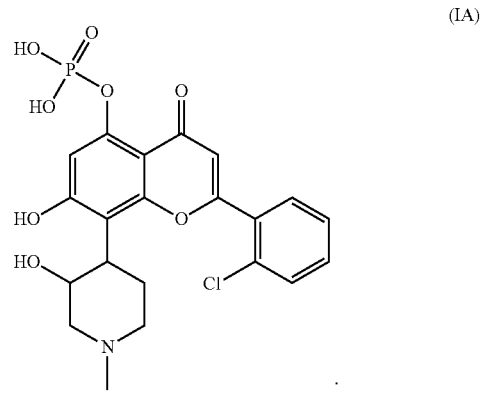 [SMILES: CN1CCC(c2c(O)cc(OP(=O)(O)O)c3c(=O)cc(-c4ccccc4Cl)oc23)C(O)C1]

4. The compound of claim 3, having the following structure (IA'):

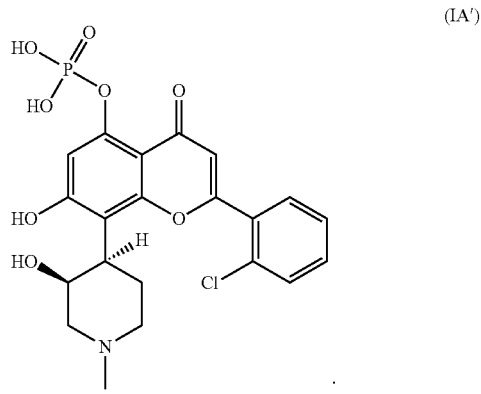 [SMILES: CN1CC[C@H](c2c(O)cc(OP(=O)(O)O)c3c(=O)cc(-c4ccccc4Cl)oc23)[C@H](O)C1]

5. The compound of claim 1, having the following structure (IB):

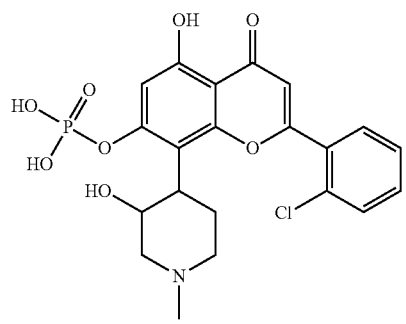

6. The compound of claim 5, having the following structure (IB'):

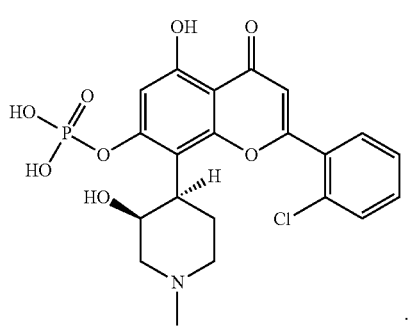

(IB')

7. The compound of claim 1, having the following structure (IC):

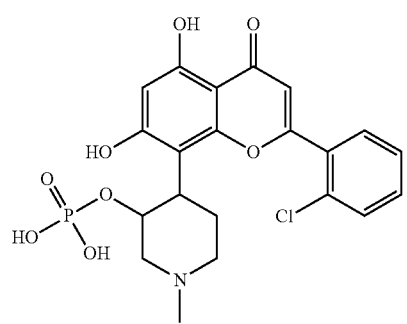

(IC)

8. The compound of claim 7, having the following structure (IC'):

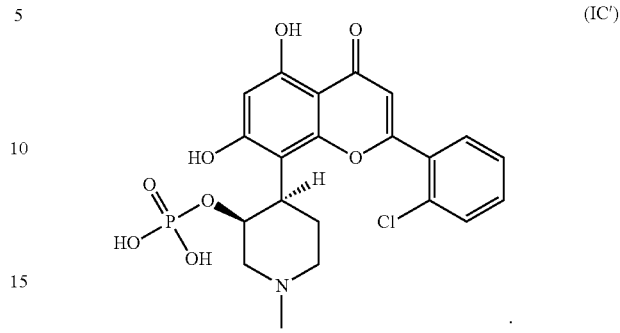

(IC')

9. A pharmaceutically acceptable salt of a compound according to claim 1.

10. The pharmaceutically acceptable salt of claim 9, wherein the pharmaceutically acceptable salt is a base addition salt.

11. The pharmaceutically acceptable salt of claim 10, wherein the pharmaceutically acceptable salt is a sodium salt.

12. The pharmaceutically acceptable salt of claim 9, wherein the pharmaceutically acceptable salt is an acid addition salt.

13. The pharmaceutically acceptable salt of claim 12, wherein the pharmaceutically acceptable salt is a hydrochloride salt.

* * * * *